(12) United States Patent
Galley et al.

(10) Patent No.: US 10,508,107 B2
(45) Date of Patent: Dec. 17, 2019

(54) MORPHOLINE DERIVATIVE

(71) Applicant: Hoffmann-La Roche Inc., Little Falls, NJ (US)

(72) Inventors: Guido Galley, Basel (CH); Marius Hoener, Basel (CH); Roger Norcross, Basel (CH); Philippe Pflieger, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/130,881

(22) Filed: Sep. 13, 2018

(65) Prior Publication Data

US 2019/0010148 A1 Jan. 10, 2019

Related U.S. Application Data

(63) Continuation of application No. PCT/EP2017/055885, filed on Mar. 14, 2017.

(30) Foreign Application Priority Data

Mar. 17, 2016 (EP) .................................... 16160790

(51) Int. Cl.
| | | |
|---|---|---|
| C07D 413/12 | (2006.01) |
| A61P 25/28 | (2006.01) |
| A61P 25/22 | (2006.01) |
| A61P 3/04 | (2006.01) |
| A61P 3/10 | (2006.01) |
| A61P 9/12 | (2006.01) |
| A61P 25/24 | (2006.01) |
| A61P 25/08 | (2006.01) |
| A61P 25/06 | (2006.01) |

(52) U.S. Cl.
CPC ............. *C07D 413/12* (2013.01); *A61P 3/04* (2018.01); *A61P 3/10* (2018.01); *A61P 9/12* (2018.01); *A61P 25/06* (2018.01); *A61P 25/08* (2018.01); *A61P 25/22* (2018.01); *A61P 25/24* (2018.01); *A61P 25/28* (2018.01)

(58) Field of Classification Search
CPC ........ C07D 413/12; A61P 25/06; A61P 25/08; A61P 25/22; A61P 25/24; A61P 25/28; A61P 3/04; A61P 3/10; A61P 9/12
See application file for complete search history.

(56) References Cited

U.S. PATENT DOCUMENTS

| | | |
|---|---|---|
| 2,161,938 A | 6/1939 | Sonn |
| 2,457,047 A | 12/1948 | Kyrides |
| 2,731,471 A | 1/1956 | Synerholm et al. |
| 2,744,909 A | 5/1956 | Speeter |
| 2,744,910 A | 5/1956 | Speeter |
| 2,778,836 A | 1/1957 | Morren |
| 2,919,274 A | 12/1959 | Faust et al. |
| 3,161,653 A | 12/1964 | Fruhstorfer et al. |
| 3,354,175 A | 11/1967 | Fruhstorfer et al. |
| 3,377,247 A | 4/1968 | Eble |
| 3,459,763 A | 8/1969 | Gruenfeld et al. |
| 3,480,630 A | 11/1969 | Stahle et al. |
| 3,577,415 A | 5/1971 | Cale, Jr. |
| 3,577,428 A | 5/1971 | Suh et al. |
| 3,586,695 A | 6/1971 | Wysong et al. |
| 3,622,579 A | 11/1971 | Stahle et al. |
| 3,660,423 A | 2/1972 | Wysong et al. |
| 3,758,476 A | 9/1973 | Ripple et al. |
| 3,818,035 A | 6/1974 | Binon et al. |
| 3,818,094 A | 6/1974 | Stahle et al. |
| 3,981,814 A | 9/1976 | Nikawitz |
| 3,992,403 A | 11/1976 | Roebke |
| 4,125,620 A | 11/1978 | Stahle et al. |
| 4,146,647 A | 3/1979 | Lafon |
| 4,311,840 A | 1/1982 | Condon |
| 4,323,570 A | 4/1982 | Stenzel et al. |

(Continued)

FOREIGN PATENT DOCUMENTS

| | | |
|---|---|---|
| CA | 962273 A | 2/1975 |
| CA | 2246027 | 2/2000 |

(Continued)

OTHER PUBLICATIONS

ISR and Written Opinion of PCT/EP2017/055885 (Completed on Apr. 4, 2017).
U.S. Appl. No. 12/028,028, dated Dec. 16, 2009, Decoret et al.
U.S. Appl. No. 12/558,772, dated Feb. 8, 2008, Decoret et al.
U.S. Appl. No. 12/639,076, dated Dec. 16, 2009, Decoret et al.
Written Opinion for Corres. PCT/EP2010/070045 dated Dec. 21, 2011.
Abdollahi-Alibeik et al., Bioorg. Med. Chem. Lett. 14:6079-6082 (2004).
Abramovitch et al., Journal of Organic Chemistry 48(23):4391-4393 (1983).

(Continued)

*Primary Examiner* — Timothy R Rozof
(74) *Attorney, Agent, or Firm* — Mark D. Kafka

(57) ABSTRACT

The present invention relates to a compound of formula

I

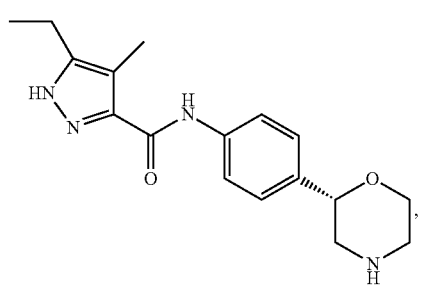

and to a pharmaceutically suitable acid addition salt thereof with a good affinity to the trace amine associated receptors (TAARs), especially for TAAR1, for the treatment of certain CNS diseases.

22 Claims, No Drawings

(56) References Cited

U.S. PATENT DOCUMENTS

| | | |
|---|---|---|
| 4,636,504 A | 1/1987 | Rossy et al. |
| 4,665,095 A | 5/1987 | Winn et al. |
| 4,735,959 A | 4/1988 | Grell et al. |
| 5,135,949 A | 4/1992 | Van Der Saal et al. |
| 5,658,938 A | 8/1997 | Geerts et al. |
| 5,610,174 A | 11/1997 | Craig et al. |
| 6,184,242 B1 | 2/2001 | Bley et al. |
| 6,268,389 B1 | 7/2001 | Esser et al. |
| 6,331,541 B1 | 12/2001 | Ko et al. |
| 6,355,660 B1 | 3/2002 | Ricks et al. |
| 6,444,686 B1 | 9/2002 | Ko et al. |
| 6,552,022 B1 | 4/2003 | Daugan |
| 6,777,428 B1 | 8/2004 | Krushinski, Jr. et al. |
| 6,794,380 B2 | 9/2004 | Brown |
| 7,351,719 B2 | 4/2008 | Stenkamp et al. |
| 7,473,698 B2 | 1/2009 | Marzabadi et al. |
| 7,569,536 B2 | 8/2009 | Hagiwara et al. |
| 7,569,583 B2 | 8/2009 | Schwink et al. |
| 7,659,394 B2 | 2/2010 | Barta et al. |
| 7,924,185 B2 | 4/2011 | Fukuhisa |
| 8,013,163 B2 | 9/2011 | Wyatt et al. |
| 8,318,735 B2 | 11/2012 | Shipps, Jr. et al. |
| 8,440,693 B2 | 5/2013 | Berghausen et al. |
| 8,716,252 B2 | 5/2014 | Schafer et al. |
| 9,452,980 B2 | 9/2016 | Groebke Zbinden et al. |
| 9,790,230 B2 * | 10/2017 | Cecere ............... C07D 491/08 |
| 10,183,933 B2 | 1/2019 | Aronov et al. |
| 2002/0019390 A1 | 2/2002 | Wong et al. |
| 2003/0105135 A1 | 5/2003 | Bovy et al. |
| 2003/0181354 A1 | 9/2003 | Abdulrazik |
| 2003/0236274 A1 | 12/2003 | Tasaka et al. |
| 2004/0157849 A1 | 8/2004 | Lee et al. |
| 2004/0235888 A1 | 11/2004 | Yamamori et al. |
| 2006/0111392 A1 | 5/2006 | Wood et al. |
| 2007/0099919 A1 | 3/2007 | Rana |
| 2007/0249620 A1 | 10/2007 | Kurata et al. |
| 2007/0254894 A1 | 11/2007 | Kane et al. |
| 2008/0076760 A1 | 3/2008 | Ohtake |
| 2008/0119535 A1 | 5/2008 | Galley et al. |
| 2009/0036420 A1 | 5/2009 | Galley et al. |
| 2009/0036452 A1 | 5/2009 | Galley et al. |
| 2009/0163545 A1 | 6/2009 | Goldfarb |
| 2009/0093497 A1 | 9/2009 | Bolin et al. |
| 2009/0306077 A1 | 10/2009 | Mogi et al. |
| 2010/0311798 A1 | 12/2010 | Decoret et al. |
| 2011/0152245 A1 | 6/2011 | Groebke Zbinden et al. |
| 2016/0264596 A1 | 9/2016 | Groebke Zbinden et al. |

FOREIGN PATENT DOCUMENTS

| | | |
|---|---|---|
| CA | 2516118 | 8/2004 |
| CH | 609558 | 3/1979 |
| CN | 101434570 | 5/2009 |
| DE | 842065 | 6/1952 |
| DE | 1083803 | 6/1960 |
| DE | 1964510 | 7/1970 |
| DE | 1795517 | 2/1972 |
| DE | 2203373 | 8/1972 |
| DE | 2 123 243 | 11/1972 |
| DE | 2123246 | 11/1972 |
| DE | 2253555 | 11/1972 |
| DE | 2446758 | 4/1976 |
| DE | 2849537 | 5/1980 |
| DE | 3133887 | 3/1983 |
| DE | 3830054 | 3/1990 |
| EP | 0024829 | 3/1981 |
| EP | 0086043 | 8/1983 |
| EP | 0125410 | 11/1984 |
| EP | 0166937 | 1/1986 |
| EP | 0167459 | 1/1986 |
| EP | 0331374 | 9/1989 |
| EP | 0392929 | 10/1990 |
| EP | 0424059 | 4/1991 |
| EP | 661266 | 12/1994 |
| EP | 0717037 | 6/1996 |
| EP | 0 748 800 A2 | 12/1996 |
| EP | 440195 B1 | 7/1997 |
| EP | 0857483 | 8/1998 |
| EP | 0924209 | 6/1999 |
| EP | 1103243 | 5/2001 |
| EP | 1413576 | 4/2004 |
| EP | 1505068 A1 | 2/2005 |
| EP | 2009005 | 12/2008 |
| EP | 2 351 744 | 8/2011 |
| EP | 2401275 B1 | 7/2013 |
| ES | 323985 | 12/1966 |
| FR | 1355049 | 3/1964 |
| FR | 6551 | 12/1968 |
| GB | 877306 | 9/1961 |
| GB | 1016514 | 5/2002 |
| JP | 61-233678 | 10/1986 |
| JP | H09-100269 A | 4/1997 |
| JP | 2001-505213 A | 4/2001 |
| JP | 2001151742 | 6/2001 |
| JP | 2004-508361 A | 3/2004 |
| JP | 2006-523692 A | 10/2006 |
| JP | 2007-051121 | 3/2007 |
| JP | 2007-191471 | 8/2007 |
| JP | 2008-179624 | 7/2008 |
| JP | 2009-539938 A | 11/2009 |
| JP | 2009-541432 A | 11/2009 |
| JP | 2010241764 | 10/2010 |
| WO | 1996/22768 | 8/1996 |
| WO | 97/12874 A1 | 4/1997 |
| WO | 98/06697 | 2/1998 |
| WO | 1998/12183 | 3/1998 |
| WO | 98/24764 | 6/1998 |
| WO | 99/09024 | 2/1999 |
| WO | 99/09024 A1 | 2/1999 |
| WO | 1999/65499 | 12/1999 |
| WO | 2000/026191 A1 | 5/2000 |
| WO | 2000/69849 A1 | 11/2000 |
| WO | 01/30762 | 5/2001 |
| WO | 2001/81334 | 11/2001 |
| WO | 02/20501 A2 | 3/2002 |
| WO | 2002/22801 | 3/2002 |
| WO | 2002/40453 | 5/2002 |
| WO | 2002/053544 | 7/2002 |
| WO | 2002/059080 | 8/2002 |
| WO | 02/076950 A2 | 10/2002 |
| WO | 2003/092374 | 11/2003 |
| WO | 03/101444 A1 | 12/2003 |
| WO | 03101444 | 12/2003 |
| WO | 2004/014898 | 2/2004 |
| WO | 2004/039764 | 5/2004 |
| WO | 2004/056774 | 7/2004 |
| WO | 2004073634 | 9/2004 |
| WO | 2004/094380 A1 | 11/2004 |
| WO | 2005/014554 | 2/2005 |
| WO | 2005/032493 A2 | 4/2005 |
| WO | 2005/040166 | 5/2005 |
| WO | 2005/046683 A1 | 5/2005 |
| WO | 2005/087217 | 9/2005 |
| WO | 2005/105763 A1 | 11/2005 |
| WO | 2006/004200 A1 | 1/2006 |
| WO | 2006009741 | 1/2006 |
| WO | 2006018662 | 2/2006 |
| WO | 2006/051851 A1 | 5/2006 |
| WO | 2006/077424 A1 | 7/2006 |
| WO | 2006/077425 | 7/2006 |
| WO | 2006070878 | 7/2006 |
| WO | 2006/107923 | 10/2006 |
| WO | 2007/03967 | 1/2007 |
| WO | 2007/017728 | 2/2007 |
| WO | 2007/024944 | 3/2007 |
| WO | 2007031791 | 3/2007 |
| WO | 2007/064818 | 6/2007 |
| WO | 2007/085556 | 8/2007 |
| WO | 2007144400 | 12/2007 |
| WO | 2008/000729 | 1/2008 |
| WO | 2008/054702 A1 | 5/2008 |
| WO | 2008/058033 A2 | 5/2008 |
| WO | 2008/092785 | 8/2008 |
| WO | 2008/098857 | 8/2008 |

(56) References Cited

FOREIGN PATENT DOCUMENTS

| WO | 2008/141976 A1 | 11/2008 |
|---|---|---|
| WO | 2008/148868 A8 | 12/2008 |
| WO | 2008148849 | 12/2008 |
| WO | 2008153959 | 12/2008 |
| WO | 2009055519 | 4/2009 |
| WO | 2010/010014 | 1/2010 |
| WO | 2006/119411 | 3/2010 |
| WO | 2010111711 | 9/2010 |
| WO | 2010/118347 A2 | 10/2010 |
| WO | 2011/076678 | 6/2011 |
| WO | 2010/097410 A1 | 1/2012 |
| WO | 2013/030252 A1 | 3/2013 |
| WO | 2012/168260 A1 | 12/2013 |
| WO | 2015/165835 A1 | 11/2015 |
| WO | 2016/016292 A1 | 2/2016 |

OTHER PUBLICATIONS

ACS (CASREACT),:1-3 (Apr 24, 2007).
Agami et al., Tetrahedron 57(1):195-200 (2001).
Altenbach et al., J. Med. Chem. 47:3220-3235 (2004).
Amemiya et al., J. Med. Chem. 35:750-755 (1992).
Amemiya et al., Synth. Commun. 20:2483-2489 (1990).
Anderson et al., "Tetrahedron" 58:8475-8481 (2002).
Armer et al., J. Exp. Opin. Ther. Patents 11(4):563-572 (2001).
Axelrod et al. Psychopharmacology Series, Trace Amines and the Brain USDIN, E.; Sandler, M., Marcel Dekker, Inc., vol. 1:1-128 (1976).
Bagley et al., Medicinal Chemistry Research 4:346-364 (1994).
Beaver et al., Journal of the American Chemical Society 79:1236-1245 (1957).
Bergeron et al., Proc. Nat!. Acad. Sci. USA 95:15730-15734 (1998).
Bestmann et al., Liebigs Ann. Chem. (Including English translation of abstract),:2061-2071 (1980).
Blanco-Pillado et al., CAPLUS AN 2004:927173.
Bliss et al., Nature 361:31-39 (1993).
Bolin et al., CAPLUS AN 2010:757048.
Botros et al., CAPLUS AN 1990:235261.
Branchek et al., "Trace amine receptors as targets for novel therapeutics: legend, myth and fact" Current Opinion in Pharmacology 3:90-97 (2003).
Buckley et al., "IRAK-4 inhibitors. Part 1: A series of amides" Bioorganic & Medicinal Chemistry Letters, 18(11):3211-3214 (2008).
Bunzow et al., Molecular Pharmacology 60:1181-1188 (2001).
Burn, "Alkylation with the Vilsmeier reagent" Bulletin de Ia Societe Chimique de France 3:848-858 (1965).
Cahiez et al., Synthesis:2138-2144 (1999).
Campos et al., Heterocycles 40:841-849 (1995).
Carlsson et al., "Interactions Between Monoamines, Glutamate, and Gaba in Schizophrenia: New Evidence" Annu. Rev. Pharmacol. Toxicol. 41:237-260 (2001).
Carlsson, J Neural Trans. 105:525-535 (1998).
Carroll et al., Med. Chem. Res. 13:134-148 (2004).
Castellanos et al., "Neuroscience of Attentiondeficit/Hyperactivity Disorder: The Search for Endophenotypes" Nat. Rev. Neurosci. 3:617-628 (2002).
Chan et al., (Chan et al., CAPLUS AN 1999:139841),:139841 (1999).
Chase et al., "The synthesis of some potential antibacterial agents" Journal of Pharmacy and Pharmacology 16(3):163-173 (1964).
Chemical Abstract XP-002435251.
Chemical Abstract XP-002435252.
Chemical Abstract XP-002436293.
Chen et al., "Copper-Catalyzed One-Pot Multicomponent Coupling Reaction of Phenols, Amides, and 4-Bromphenyl Iodide" Organic Letters 10(20):4565-4568 (2008).
Chen et al., J Neurophysiol. 89(2):691-703 (2003).
Clark et al., Journal of Medicinal Chemistry 29(8):1534-1537 (1986).

Clinical Trial, 2011, http://www.nature.com/news/2011/110928/full/477526a.html.
Clitherow et al., J. Med. Chern. 37(15):2253-2257 (1994).
Cordi et al., Journal of Med. Chem. 44(50):787-805 (2001).
Dash et al., J. Heterocyclic Chem.:401-404 ( 2006).
DeBarnardis et al., "Conformationally Defined Adrenergic Agents. 5. Resolution, Absolute Configuration, and Pharmacological Characterization of the Enantiomers of 2-(5,6-Dihydroxy-1,2,3,4-tetrahydro-l-naphthyl)imidazoline: A Potent Agonist at a-Adrenoceptorst" J. Med. Chem. 30:1011-1017 (1987).
DeBernardis et al., J. Med. Chem. 29:1413-1417 (1986).
Delucca et al., Journal of Medicinal Chemistry 45:3794-3804 (2002).
DeRuiter et al., "Synthesis and in Vitro Aldose Reductase Inhibitory Containing an N-Acylglycine Moiety" J. Med. Chem. 32:1033-1038 Activity of Compounds (1989).
Deutch et al. Neurotransmitters in Fundamental Neuroscience "Chapter 8 Neurotransmitters"2nd edition, Academic Press,:193-234 (1999).
Dias et al., J. Med. Chem. 40:1206-1213 (2005)
Du Pont, CAPLUS AN, 1966:465238.
Dyck, L. E., "Release of Some Endogenous Trace Amines From Rat Striatal Slices in the Presence and Absence of a Monoamine Oxidase Inhibitor" Life Sciences 44:1149-1156 (1989)
English Abstract Corresponding to B1 (DE 842065), Lehmann et al. entitled, "N-Containing heterocyclic compounds.", pp. 1 (2007)
English translation of the Chinese Office Action, dated Oct. 11, 2018, in the related Chinese Application No. 201510671612.8. (dated Oct. 11,2018).
English translation of the Japanese Office Action, dated Jan. 10, 2017, in the related Japanese patent application No. 2015-218849. (dated Jan. 10, 2017).
English translation of the Japanese Office Action, dated Mar. 4, 2014, in corresponding Japanese Application No. 2012-545252.
English translation of the Japanese Office Action, dated Jul. 31, 2018, in the related Japanese Appl. No. 2015-218849. (dated Jul 31,2018).
European Office Action, dated Aug. 8, 2018, in related European Application No. 17151744.4. (dated Aug 8,2018).
Evans et al., "Tetrahedron Lett." 39:2937-2940 (1998).
F. Manetti et al., "Building a pharmacophore model for a novel class of antitubercular compounds," II Farmaco, vol. 55, Issues 6-7, Jul. 2000, pp. 484-491.
Faust et al., J. Org. Chem. 26:4044-4047 (1961).
Flippin et al., Tetrahedron Letters 34:3255-3258 (1993).
Freiter, E.R. et al., J. Heterocyclic Chem. 10:391-394 (1973).
Fujioka et al., Tetrahedron Lett. 46:2197-2199 (2005).
Gainetdinov et al., Trends in Pharm. Sci. 23(8):367-3'13 (2002).
Gentili et al., J. Med. Chem. 47:6160-6173 (2004).
Gilbert et al., Journal of the Chemical Society:2323-2331 (1931).
Goldfarb, 2009, CAPLUS AN 2009:846103, pp. 846103 (2009).
Goldfarb, CAPLUS AN 2009:846114.
Goldfarb-2, 2009, CAPLUS AN 2009:846107, pp. 846107 (2009).
Goldfarb-3, 2009, CAPLUS AN 2009:846105, pp. 846105 (2009).
Goldfarb-4, 2009, CAPLUS AN 2009:846104, pp. 846104.
Graeheva et al., "Reduction of quinolinecarboxylic acids by raney alloy" Chemistry of Heterocyclic Compounds (English translation of Khimiya Geterotsiklicheskikh Soedinenii, No. i, pp. 77-79, Jan., 1988), 24(1):6567 (1988).
Griffith et al., Journal of the Chemical Society 127:990-995 (1925).
Habib et al. Synthesis "Synthesis Communications":825-827 (1984).
Heinicke et al., Australian Journal of Chemistry 37(4):831-44 (1984).
Hirashima et al., Bioorganic & Medicinal Chemistry 10:117-123 (2002).
Hlasta et al., J. Med. Chem. 30:1555-1562 (1987).
Holt, "Imidazoline binding sites on receptors and enzymes: Emerging targets for novel antidepressant drugs?" J. Psychiatry Neurosci., 28(6):409-414 (2003).
Hong et al., Taehan Hwahakhoe Chi 17(3):193-197 (1973).
Hosseinzadeh et al., "Copper-catalyzed arylation of phenylurea using KF/A1203" Tetrahedron letters 49:840-843 (2008).
Huh et al., Tetrahedron 58:9925-9932 (2002).
Huh et al., Tetrahedron 60:9857-9862 (2004).

(56) References Cited

OTHER PUBLICATIONS

International Search Report dated Mar. 1, 2011 in corresponding PCT Application PCT/EP2010/070045 (dated Mar 1,2011).
Ishihara et al., Synlett:227-230 (2006).
Ito et al., J. Pesticide Sci. 10(4):697-702 (1985).
Jackson et al., Perkin Transactions 1 2:205-210 (2000).
Javitt et al., Bioi. Psychiatry 45:668-679 (1999).
Jetter et al., "Synthesis":829-831 (1998).
Katritzky et al., Journal of Organic Chemistry 71(9):3375-3380 (2006).
Katz et al., "A synthesis of some pyridinylpyrimidines from ketenedithioacetals," Tetrahedron, v. 45, No. 6.—p. 1801-1814 (1989).
Kim et al., Journal of Combinatorial Chemistry 4(6):549-551 (2002).
Kim et al., "Synthesis and structure-actitivity studies of novel homomorpholine oxazolidinone antibacterial agents" Bioorganic & Medicinal Chemistry Letters (Cited in P26295-JP, JP-1), 19:550-553 (2009).
Klapars et al., J. Am. Chem. Soc. 123:7727-7729 (2001).
Klemm, Journal of Organic Chemistry 23:349-353 (1958).
Kobs et al., Chernische Berichte 123(11):2191-2194 (1990).
Kornicka et al., Heterocycles 68:687-699 (2006).
Kosasayama et al., Chem. Pharm. Bull. 27:27 (1979).
Kumar et al., Journal of Medicinal Chemistry 27(8):1083-1089 (1984).
Law et al., J. Med. Chem. 41:2243-2251 (1998).
Lee et al., "4-[(N-imidazol-2-ylmethyl)aniline]pyranopyridine analogs as novel anti-angiogenic agents." Bull Korean Chem. Soc. 25:619-628 (2005).
Lee et al., "Kinetics and Mechanism of the Aminolysis of Benzoic Anhydrides" Journal of Physical Organic Chemistry 7(6):273-279 (1994).
Lee et al., Macromolecular Rapid Communications 23(12):665-671 (2002).
Lewis et al., Neuron. 28:325-334 (2000)).
Li et al., "Design and Synthesis of 5-Aryl-pyridone-carboxamides as Inhibitors of Anaplastic Lymphoma Kinase," J. Med. Chem. 2006, 49, 1006-1015.
Li et al., CAPLUS AN 2006:49622.
Lindemann et al., "A renaissance in trace amines inspired by a novel GPCR family" TREANDS in Pharmacological Sciences 26(5) (May 2005).
Lindermann et al., "Trace amine-associated receptors form structurally and functionally distinct subfamilies of novel G protein-coupled receptors" Genomics 85:372-385 (2005).
Lloyd et al. vol. 36:2675-2679 (1980).
Lopez-Corcuera et al., Mol. Mem. Biol. 18:13-20 (2001).
Mancuso et al., J. Org. Chem. 43:2480-2482 (1978).
Matsunaga et al., "Bioorganic & Medicinal Chemistry" (XP002444990),:4314-4336 (2004).
Matsunaga et al., Tetrahedron:Asymmetry 15:2021-2028 (2004).
McCormack et al., "Autoradiographic Localization of Tryptamine Binding Sites in the Rat and Dog Central Nervous System" The Journal of Neuroscience 6(1):94-101 (Jan. 1986).
McLennan, P.L., "European Journal of Pharmacology" 69:477-482 (1981).
Mehrotra et al., Tetrahedron Letters 4:321-322 (1971).
Melloni et al., Eur. J. Med. Chem 26:207-213 (1991).
Mitsutake et al., Journal of Agricultural and Food Chemistry 34:725-733 (1986).
Mohammadpoor-Baltork, Bull. Korean Chem. Soc. 24:1354-1356 (2003).
Mohammadpoor-Baltork, Synlett:2803-2805 (2004).
Mohn et al., Cell 98:427-436 (1999).
Moormann et al., J. Med. Chem.:614-626 (1990).
Morgan et al., Synthesis of Ant. Homologues (2323).
Mosseau et al. Progress in Brain Research "Chapter 29 A high-affinity [3H]tryptamine binding site in human brain" Peter M. Yu, et al., Elsevier Ltd, vol. 106:285-291 (1995).
Nakamoto et al., CAPLUS AN 2005:324138.
Nakamura et al., J. Chem. Soc. Perkin Trans 1:1061-1066 (2002).
Nakazato et al., "Exp. Opin. Ther. Patents" 10(1):75-98 (2000).
Nathanson, J.A., Amer. Soc. Pharmacology 28:254-268 (1985).
Ohta, Chem. Pharm. Bull. 35:1058-1069 (1987).
Ohta, Synthesis:78-81 (1990).
Ojida et al., Org. Letters:3051-3054 (2002).
Ojida et al., "Tetrahedron Asymmetry" 15:1555-1559 (2004).
Olah, Synlett:647-650 (1992).
Olmos et al., European Journal of Pharmacology 262:41-48 (1994).
Parker et al., J. Pharmacol. Exp. Ther. 245:199-210 (1988).
Parkinsons treatment, 2012, http://health.nytimes.com/health/guides/disease/parkinsons-disease/overview.htmi#Treatment.
Parkinsons-prevention, 2012, http://www.webmd.com/parkinsons-disease/guide/parkinsons-disease-prevention.
Partridge et al., "Journal of the Chemical Society":3043-3046 (1949).
Patani et al., Chem. Rev. 96:3147-3176 (1996).
Perner et al., Journal of Medicinal Chemistry 50(15):3651-3660 (2007).
Perry et al., Journal of Orgamc Chemistry 61(21):7482-7485 (1996).
Pieter et al., "Correlations Between Central Hypotensive and Peripheral Hypertensive Effects of Structurally Dissimilar Alpha-Adrenoceptor Agonists" Life Sciences (XP-002442517), 28:653-660 (1981).
Pigini et al., Eur. J. Med. Chem. 22:273-276 (1987).
Pinza et al., Heterocycles 4:1699-1706 (1976).
Pralong et al., "Cellular perspectives on the glutamate-monoamine interactions in limbic lobe structures and their relevance for some psychiatric disorders" Prog. in Neurobiol. 67:173-202 (2002).
Premont et al., "Following the trace of elusive amines" Proc. Natl. Acad. Sci. USA 98(17):9474-9475 (2001).
Prisinzano et al., Bioorganic & Medicinal Chemistry Letter 14:4697-4699 (2004).
Raddatz, Rita et al., J. Pharmacol. Exp. Therap. 292:1135-1145 (2000).
Registry No. 1017367-32-6 (Apr. 25,2 008).
Registry No. 794559-77-6 (Dec. 8, 2004).
Reimann et al., "Intramolekulare Aromatena lierungen, 25.Mitt. Zur Synthese von Hexahydro-7H-naphtho[1,8-fg]chinolinen und -isochinolinen," Arch. Pharm., 322:363-367 (1989) with English abstract.
RN346639-43-8, registry database compound (Jul. 18, 2001).
RN543694-11-7, registry database compound (Jul. 7,2003).
RN543694-11-7-pubchem, pubchem record for RN 543694-11-7 (2005).
Robertson et al., J. Med. Chem. 29:1577-1586 (1986).
Saunders et al., "The Thermal Rearrangement of Triatylmethyl Azides" (Contribution from the Department of Chemistry, University of Rochester), 80:3328-3332 (1958).
Savola et al., "Cardiovascular and Sedative Alpha-Adrenoceptor Effects of Detomidine-Like Arylalkyl Imidazoles and Associated Derivatives", Arzneimittel_Forschung/Drug Research, 38:29-35 (1988).
Schollkopf et al. et al., "Enantioselective Synthesis of (R)-Amino Acids Using L-Valine as Chiral Agent" Angew Chem Int Ed Engl 20:798-799 (1981).
Selinger et al., "Determination of encainide and its metabolites by high-performance liquid chromatography" Journal of Pharmaceutical and Biomedical Analysis (Cited in P26295-JP, JP-1), 7(3):355-359 (1989).
Shafiee et al., J. Heterocyclic Chem. 35:607-610 (1998).
Sharma, Br. J. Psychiatry 174(Suppl 38):44-51 (1999).
Shi et al., Journal of Medicinal Chemistry 39(17):3375-3384 (1996).
Srivastava et al., Agricultural and Biological Chemistry 40(1):213-214 (1976).
Strieter et al., "Mechanistic Studies on the Copper-Catalyzed N-Arylation of Amides" J. Am. Chem. Soc. 131:78-88 (2009).
Sugiyama et al., CAPLUS AN 1985:131916.
Tang et al., Nature 401:63-69 (1999).
Tarnchompoo, B. et al., 31:5779-5780 (1990).
The Australian Examination Report, dated Jan. 22, 2016, in the corresponding Australian application No. 2010335277.
The English translation of the Japanese Office Action, dated Jan. 20, 2015, in the corresponding Japanese Application No. 2012-545252.

(56) References Cited

OTHER PUBLICATIONS

The European Communication, dated Mar. 31, 2015, in the corresponding European application No. 10793256.8.
The European Communication, dated Oct. 22, 2015, in the corresponding European application No. 10793256.8.
Timmermans et al., Life Sciences 28:653-660 (1981).
Tomita et al., CAPLUS AN 1995:305181.
Touzeau et al., "Synthesis and Biological Evaluation of New 2-(4,5-Dihydro-1H-imidazol-2-yl)-3,4-dihydro-2H-1,4-benzoxazine Derivatives" J. Med. Chem. 46:1962-1979 (2003).
Trani et al., "Synthesis of 2-Chloro-2-imidazoline and its Reactivity with Aromatic Amines, Phenols, and Thiophenols" Heterocycl. Chem. 11:257-262 (Apr. 1974)
Tuite et al., "Recent developments in the pharmacological treatment of Parkinson's disease" Expert Opin. Investig. Drugs 12:1335-1352 (2003).
Ueda et al., Bioorganic & Medicinal Chem. Letters 14(Suppl 2):313-316 (2004).
Ugi et al. Isonitrile XVII "Addition Von Rhodanwasserstoffsaure an Isonitrile", Liebigs, Ann. Chem. 80:80-82 (1963).
Ugi et al., "Isonitrilet XVIII. 'Hydantoin~imide-(4)", Chemische Berichte, v. 97, Issue 8, Aug. 1964, pp. 2276-2281.
Vandenberg et al., Exp. Opin. Ther. Targets 5(4):507-518 (2001).
Vassiliou et al., Synlett:2398-2400 (2003).
Verma et al., "Indolyl Compounds 358-363, 1982. as Antiinflammatory Agents," Arch. Pharm. vol. 315, pp. 358-363, 1982.
Waisser et al., Magnetic Resonance in Chemistry 35(8):543-548 (1997).
Waisser et al., Pharmazie 53(3):193-195 (1998).
Wentland et al., "Synthesis and Antidepressant Properties of Novel 2-Substituted 4,5-Dihydro-1H-imidazole Derivatives" J. Med. Chem 30:1482-1489 (1987).
White, Pesticide Biochemistry and Physiology 34(3):255-276 (1989).
Wilkinson et al., Biochemical Pharmacology 21:3187-3192 (1972).
Wong et al., "Research and Treatment Approaches to Depression" Nature Reviews 1Neuroscience 2:343-351 (May 2001).
Written Opinion for International Application No. PCT/EP2010/070045, pp. 7 (Dec. 21,2011).
Wu, G. et al., Synthesis 11:1657-1660 (2003).
Yoshino et al., Journal of Medicinal Chemistry 29(5):820-825 (1986).
Zhang et al., J. Med. Chem. 40:3014-3024 (1997).
Belavita et al., "CAPLUS Accession No. 1967:464364" Bazzetta Chimica Italiana:135-147 (1967)
Guo et al., "Efficient Iron-Catalyzed N-Arylation of Aryl Halides with Amines" Org. Lett 10:4513-4516 (2008).
Hideaki Yamaguchi, CAS Registry Database, 1995:549305, (From Chemical Abstracts (XP002465006 & JP 06 268356), 1994), pp. 2 1995.
Iyer et al., "Microwave-enhanced rhodium-catalyzed conjugate-addition of aryl boronic acids to unprotected maleimides" Tetrahedron Letters 48:4413-4418 (2007).
Methcohn et al., CAS Registry Database, 1963:475281 pp. 2 1963.
Methcohn et al., Journal of the American Chemical Society:4666-4669 (1963).
RN 1178288-01-1, 1-Piperazineacetamide, N-[3-(1-pyrrolidinyl)phenyl]-, pp. 1 (Aug. 31, 2009).
RN 1197570-08-3, registry database compound (Dec. 16, 2009).
Schollkopf, "Enantioselective synthesis of nonproteinogenic amino acids" Topics in Current Chemistry/Wittig Chemistry:65-84 (1983).
Wolter et al., "Copper-Catalyzed Coupling of Aryl Iodides with Aliphatic Alcohols" Org. Lett 4(6):973-976 (2002).
Yur'ev et al., "Nitration, bromation and carboxylation of N-phenylpyrrolidine" Proc. of the Academy of Sciences of USSR Dept. of Chem. Sci. (CAPLUS Accession No. 1951:60106), 2:166-171 (1951).
Zheng and Buchwald, "Copper-Catalyzed Regiospecific Synthesis of N-Alkylbenzimidazoles" Organic Letters 9(23):4749-4751 (2007).

\* cited by examiner

MORPHOLINE DERIVATIVE

CROSS-REFERENCE TO RELATED APPLICATIONS

This application is a continuation of, and claims priority to, International Patent Application No. PCT/EP2017055885, filed on Mar. 14, 2017. This application also claims priority to European Patent Application No. 16160790.8, filed on Mar. 17, 2016. The entire contents of each of the above patent applications are hereby incorporated by reference.

The present invention relates to a compound of formula

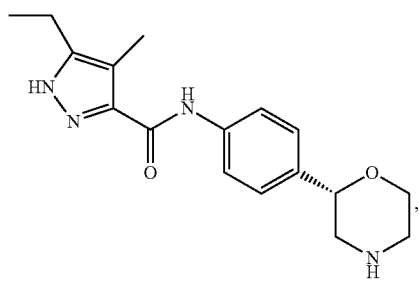

I and to a pharmaceutically suitable acid addition salt thereof.

The compound disclosed herein and covered by Formula I above may exhibit tautomerism. It is intended that the invention encompasses any tautomeric form of this compound, or mixtures of such forms, and is not limited to any one tautomeric form depicted in the formula above.

It has now been found that the compound of formula I (5-ethyl-4-methyl-N-[4-[(2S) morpholin-2-yl]phenyl]-1H-pyrazole-3-carboxamide) has a good affinity to the trace amine associated receptors (TAARs), especially for TAAR1, and less side effects compared with compounds of the prior art.

Similar ligands of mouse TAAR1 and rat TAAR1 have been disclosed in WO2011/076678 and WO2012/16826.

The compound of formula I and its pharmaceutically usable addition salts possess valuable pharmacological properties. Specifically, it has been found that the compound of the present invention is a partial agonist of the human trace amine associated receptor 1 (hTAAR1).

The compound of the present invention has significant advantages over compounds of the prior art, which advantages are potent agonistic activity at the human TAAR1 receptor,
selectivity against the dopamine transporter (DAT),
selectivity against the hERG ion channel,
a low amphiphilic vector and thereby posing a low risk of causing drug-induced phospholipidosis (DIPL) (vide infra).

The compound of formula I may therefore be used as a safe drug for the treatment of depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, addiction, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

The classical biogenic amines (serotonin, norepinephrine, epinephrine, dopamine, histamine) play important roles as neurotransmitters in the central and peripheral nervous system[1]. Their synthesis and storage, as well as their degradation and reuptake after release, are tightly regulated. An imbalance in the levels of biogenic amines is known to be responsible for the altered brain function under many pathological conditions[2-5]. A second class of endogenous amine compounds, the so-called trace amines (TAs), significantly overlaps with the classical biogenic amines regarding structure, metabolism and subcellular localization. The TAs include p-tyramine, β-phenylethylamine, tryptamine and octopamine, and they are present in the mammalian nervous system at generally lower levels than classical biogenic amines[6].

Dysregulation of TAs has been linked to various psychiatric diseases like schizophrenia and depression[7] and to other conditions like attention deficit hyperactivity disorder, migraine headache, Parkinson's disease, substance abuse and eating disorders[8,9].

For a long time, TA-specific receptors had only been hypothesized based on anatomically discrete high-affinity TA binding sites in the CNS of humans and other mammals [10,11]. Accordingly, the pharmacological effects of TAs were believed to be mediated through the well-known machinery of classical biogenic amines, by either triggering their release, inhibiting their reuptake or by "cross-reacting" with their receptor systems[9,12,13]. This view changed significantly with the identification of several members of a novel family of GPCRs, the trace amine-associated receptors (TAARs)[7,14]. There are 9 TAAR genes in human (including 3 pseudogenes) and 16 genes in mouse (including 1 pseudogene). The TAAR genes do not contain introns (with one exception, TAAR2 contains 1 intron) and are located next to each other on the same chromosomal segment. The phylogenetic relationship of the receptor genes, in agreement with an in-depth GPCR pharmacophore similarity comparison, and pharmacological data suggest that these receptors form three distinct subfamilies[7,14]. TAAR1 is in the first subclass of four genes (TAAR1-4) highly conserved between human and rodents. TAs activate TAAR1 via $G_\alpha s$. Dysregulation of TAs was shown to contribute to the aetiology of various diseases like depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, addiction, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

Therefore, there is a broad interest to increase the knowledge about trace amine-associated receptors.

Literature References

[1] Deutch, A. Y. and Roth, R. H.; "Neurotransmitters." In *Fundamental Neuroscience* (2$^{nd}$ Edn) (Zigmond, M. J., Bloom, F. E., Landis, S. C., Roberts, J. L, and Squire, L. R., Eds.), pp. 193-234, Academic Press (1999);

[2] Wong, M. L. and Licinio, J.; "Research and treatment approaches to depression." *Nat. Rev. Neurosci.* 2001, 2, 343-351;

[3] Carlsson, A. et al.; "Interactions between monoamines, glutamate, and GABA in schizophrenia: new evidence." *Annu. Rev. Pharmacol. Toxicol.* 2001, 41, 237-260;

[4] Tuite, P. and Riss, J.; "Recent developments in the pharmacological treatment of Parkinson's disease." *Expert Opin. Investig. Drugs* 2003, 12, 1335-1352;

[5] Castellanos, F. X. and Tannock, R.; "Neuroscience of attention-deficit/hyperactivity disorder: the search for endophenotypes." *Nat. Rev. Neurosci.* 2002, 3, 617-628;

[6] Usdin, Earl; Sandler, Merton; Editors; *Psychopharmacology Series, Vol. 1: Trace Amines and the Brain.* [*Proceedings of a Study Group at the 14th Annual Meeting of the American College of Neuropsychopharmacology*, San Juan, Puerto Rico] (1976);

[7] Lindemann, L. and Hoener, M.; "A renaissance in trace amines inspired by a novel GPCR family." *Trends in Pharmacol. Sci.* 2005, 26, 274-281;

[8] Branchek, T. A. and Blackburn, T. P.; "Trace amine receptors as targets for novel therapeutics: legend, myth and fact." *Curr. Opin. Pharmacol.* 2003, 3, 90-97;

[9] Premont, R. T. et al.; "Following the trace of elusive amines." *Proc. Natl. Acad. Sci. USA* 2001, 98, 9474-9475;

[10] Mousseau, D. D. and Butterworth, R. F.; "A high-affinity [$^3$H] tryptamine binding site in human brain." *Prog. Brain Res.* 1995, 106, 285-291;

[11] McCormack, J. K.; "Autoradiographic localization of tryptamine binding sites in the rat and dog central nervous system." *J. Neurosci.* 1986, 6, 94-101;

[12] Dyck, L. E.; "Release of some endogenous trace amines from rat striatal slices in the presence and absence of a monoamine oxidase inhibitor." *Life Sci.* 1989, 44, 1149-1156;

[13] Parker, E. M. and Cubeddu, L. X.; "Comparative effects of amphetamine, phenylethylamine and related drugs on dopamine efflux, dopamine uptake and mazindol binding." *J. Pharmacol. Exp. Ther.* 1988, 245, 199-210;

[14] Lindemann, L. et al.; "Trace amine associated receptors form structurally and functionally distinct subfamilies of novel G protein-coupled receptors." *Genomics* 2005, 85, 372-385.

Objects of the present invention are the new compound of formula I and its pharmaceutically acceptable salts, their use for the treatment of diseases related to the biological function of the trace amine associated receptors, their manufacture and medicaments based on the compound in accordance with the invention in the control or prevention of illnesses such as depression, anxiety disorders, bipolar disorder, attention deficit hyperactivity disorder, stress-related disorders, psychotic disorders such as schizophrenia, neurological diseases such as Parkinson's disease, neurodegenerative disorders such as Alzheimer's disease, epilepsy, migraine, substance abuse, addiction and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

The present compound of formula I and its pharmaceutically acceptable salts can be prepared by methods known in the art, for example, by processes described below, which process comprises a) cleaving off the N-protecting group (PG) from compounds of formula

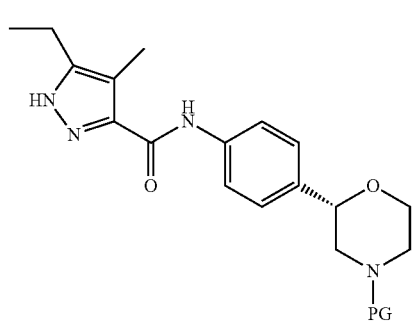

3' to a compound of formula

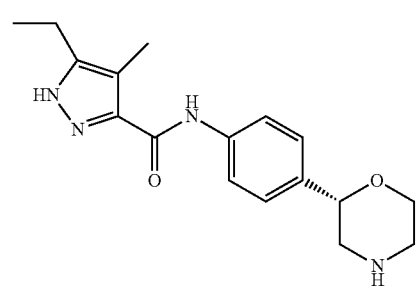 [SMILES: CCc1[nH]nc(C(=O)Nc2ccc([C@H]3CNCCO3)cc2)c1C]

I wherein PG is a N-protecting group selected from —C(O)O-tert-butyl (BOC), and, if desired, converting the compound obtained into pharmaceutically acceptable acid addition salts.

GENERAL PROCEDURE

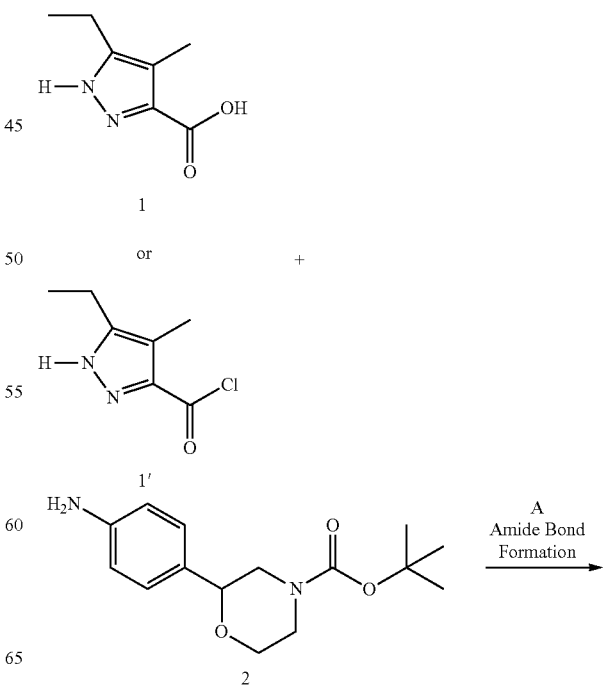

Scheme 1

-continued

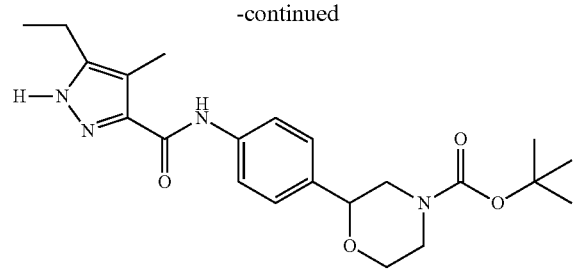

3

B
Cleavage of
protecting group

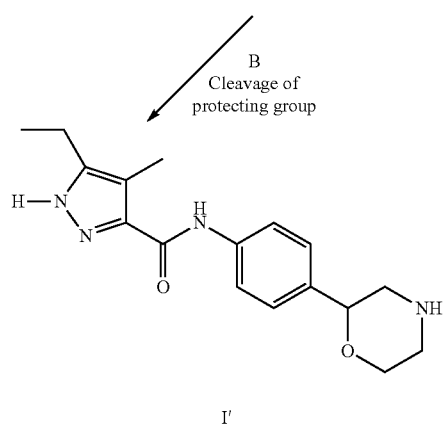

I'

The starting materials 1,1' and 2 are commercially available or may be prepared by methods well known in the art. Racemic tert-butyl 2-(4-aminophenyl)morpholine-4-carboxylate (CAS RN: 1002726-96-6) is commercially available. tert-Butyl (2R)-2-(4-aminophenyl)morpholine-4-carboxylate (CAS RN: 1260220-42-5) is commercially available. tert-Butyl (2S)-2-(4-aminophenyl)morpholine-4-carboxylate (CAS RN: 1260220-43-6) is commercially available, or can be prepared as described in the literature, for instance as described in Trussardi, R. & Iding, H, PCT Int. Appl. WO 2015/086495 A1.

Step A: Amide bond formation can be accomplished by a coupling reaction between amine 2 and carboxylic acid compound 1 in the presence of a coupling reagent such as DCC, EDC, TBTU or HATU in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF, DME or TBME.

Preferred conditions are TBTU with N-methylmorpholine in THF at 50-60° C. for 12-48 hours. Alternatively, amide bond formation can be accomplished by a coupling reaction between amine 2 and acyl chloride compound 1' in halogenated solvents such as dichloromethane or 1,2-dichloroethane or ethereal solvents such as diethyl ether, dioxane, THF, DME or TBME, in the presence of an organic base such as triethylamine or N,N-diisopropylethylamine.

Preferred conditions are triethylamine in THF at room temperature for 18 hours.

If desired, the acyl chloride compound 1' may be prepared in situ from the corresponding carboxylic acid 1 by treatment with oxalyl chloride in halogenated solvents such as dichloromethane or 1,2-dichloroethane or ethereal solvents such as diethyl ether, dioxane, THF, DME or TBME in the presence of a catalyst such as DMF.

Preferred conditions are dichloroethane at room temperature for 1 hour.

Alternatively, the acyl chloride compound 1' may be prepared in situ from the corresponding carboxylic acid 1 by treatment with 1-chloro-N,N,2-trimethylpropenylamine [CAS 26189-59-3] in dichoromethane, followed by removal of the solvent in vacuo, according to the method of Ghosez and co-workers (J. Chem. Soc., Chem. Commun. 1979, 1180; Org. Synth. 1980, 59, 26-34).

Step B: Removal of the BOC N-protecting group can be effected with mineral acids such as HCl, $H_2SO_4$ or $H_3PO_4$ or organic acids such as $CF_3COOH$, $CHCl_2COOH$, HOAc or p-toluenesulfonic acid in solvents such as $CH_2Cl_2$, $CHCl_3$, THF, MeOH, EtOH or $H_2O$ at 0 to 80° C.

Preferred conditions are $CF_3COOH$ in aqueous acetonitrile at 80° C. for 3 hours or 4 N HCl in dioxane at room temperature for 16 hours.

Where racemic starting material 2 has been used, the resulting racemic mixture of morpholine compounds I' may be separated into its constituent enantiomers by using chiral HPLC. Alternatively, compound I may be obtained in enantiomerically pure form by starting from enantiomerically pure compound 2.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC. Racemic mixtures of chiral synthetic intermediates may also be separated using chiral HPLC.

Salts of Compound of Formula I

The compound of formula I is basic and may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

EXAMPLE 1

5-Ethyl-4-methyl-N-[4-[(2S)-morpholin-2-yl]phenyl]-1H-pyrazole-3-carboxamide

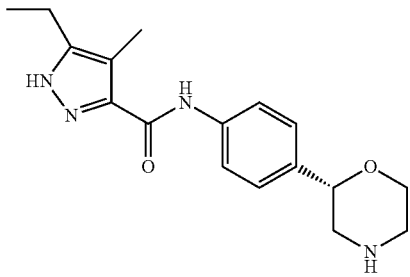

a) tert-Butyl (2S)-2-[4-[(5-ethyl-4-methyl-1H-pyrazole-3-carbonyl)amino]phenyl]morpholine-4-carboxylate To a stirred solution of tert-butyl (2S)-2-(4-aminophenyl)morpholine-4-carboxylate (CAS RN: 1260220-43-6, 350 mg, 1.26 mmol, 1.00 equiv.) and 5-ethyl-4-methyl-1H-pyrazole-3-carboxylic acid (CAS RN: 957129-38-3, 245 mg, 1.51 mmol, 1.20 equiv.) in THF (8 ml) were added TBTU (807 mg, 2.51 mmol, 2.00 equiv.) and N-methylmorpholine (509 mg, 553 µl, 5.03 mmol, 4.00 equiv.). The reaction mixture was stirred at 50° C. for 15 h. TLC at t =15 h showed the reaction was complete. The reaction mixture was concentrated in vacuo. The crude material was purified by flash chromatography (silica gel, eluant: 0% to 100% EtOAc in heptane) to afford tert-butyl (2S)-2[4-[(5-ethyl-4-methyl-1H-pyrazole-3-carbonyl)amino]phenyl]morpholine-4-carboxylate as an off-white solid (501 mg, 96%). MS (ISP): 413.7 ([M−H]−).

b) 5-Ethyl-4-methyl-N-[4-[(2S)-morpholin-2-yl]phenyl]-1H-pyrazole-3-carboxamide

To a stirred solution of trifluoroacetic acid (1.37 g, 918 µl, 12.0 mmol, 10 equiv.) in water (8 ml) was added a suspension of tert-butyl (2S)-2-[4-[(5-ethyl-4-methyl-1H-pyrazole-3-carbonyl)amino]phenyl]morpholine-4-carboxylate (497 mg, 1.2 mmol, 1.00 equiv.) in acetonitrile (4 ml). The reaction mixture was stirred at 80° C. for 3 h. MS at t=3 h showed the reaction was complete. The reaction mixture was poured into 1 M aq. NaOH and extracted twice with EtOAc. The organic layers were dried over $Na_2SO_4$ and concentrated in vacuo. The crude material was purified by flash column chromatography (SiliaSep™ amine cartridge, eluant: 0% to 100% EtOAc in heptane, then 0% to 10% MeOH in EtOAc) to afford 5-ethyl-4-methyl-N-[4-[(2S)-morpholin-2-yl]phenyl]-1H-pyrazole-3-carboxamide (327 mg, 87%) as an off-white solid. MS (ISP): 315.7 ([M+H]+).

EXAMPLE 2 (COMPARATIVE EXAMPLE)

5-Ethyl-4-methyl-N-[4-[(2R)-morpholin-2-yl]phenyl]-1H-pyrazole-3-carboxamide

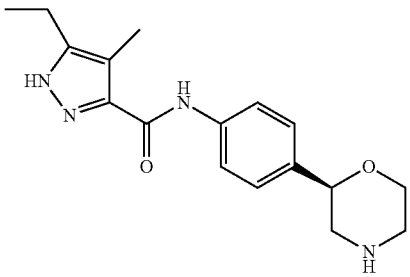 [SMILES: CCc1[nH]nc(C(=O)Nc2ccc([C@@H]3CNCCO3)cc2)c1C]

The title compound was obtained in analogy to example 1 using (2R)-2-(4-aminophenyl)morpholine-4-carboxylate (CAS RN: 1260220-42-5) in place of (2S)-2-(4-aminophenyl)morpholine-4-carboxylate in step (a). White solid. MS (ISP): 315.6 ([M+H]+).

EXAMPLE 3 (COMPARATIVE EXAMPLE )

N-[4-[(2S)-Morpholin-2-yl]phenyl]-6-(2,2,2-trifluoroethoxy)pyridine-3-carboxamide

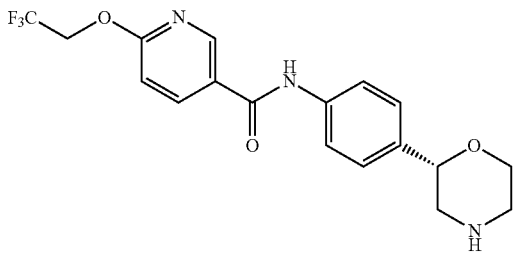 [SMILES: O=C(Nc1ccc([C@H]2CNCCO2)cc1)c1ccc(OCC(F)(F)F)nc1]

The title compound was obtained in analogy to example 1 using 6-(2,2,2-trifluoroethoxy)nicotinic acid (CAS RN: 159783-29-6) in place of 5-ethyl-4-methyl-1H-pyrazole-3-carboxylic acid in step (a). White solid. MS (ISP): 382.1 ([M+H]+).

EXAMPLE 4 (COMPARATIVE EXAMPLE)

6-Chloro-N-[4-[(2S)-morpholin-2-yl]phenyl]pyridine-3-carboxamide

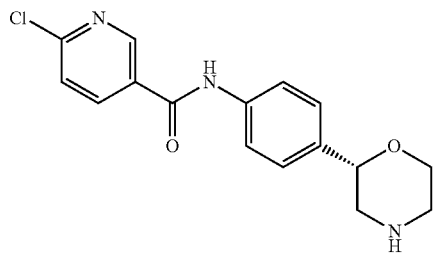 [SMILES: O=C(Nc1ccc([C@H]2CNCCO2)cc1)c1ccc(Cl)nc1]

The title compound was obtained in analogy to example 1 using 6-chloro-nicotinic acid (CAS RN: 5326-23-8) in place of 5-ethyl-4-methyl-1H-pyrazole-3-carboxylic acid in step (a). White solid. MS (ISP): 320.1 ([{$^{37}$Cl}M+H]$^+$), 318.2 ([{$^{35}$Cl}M+H]$^+$).

EXAMPLE 5 (COMPARATIVE EXAMPLE)

2-Chloro-N-[4-[(2S)-morpholin-2-yl]phenyl]pyridine-4-carboxamide

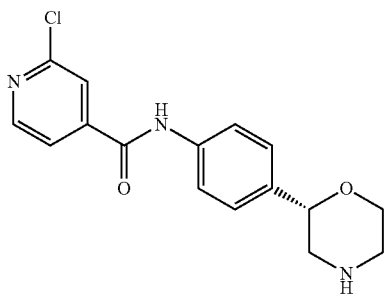 [SMILES: O=C(Nc1ccc([C@H]2CNCCO2)cc1)c1ccnc(Cl)c1]

The title compound was obtained in analogy to example 1 using 2-chloro-isonicotinic acid (CAS RN: 6313-54-8) in place of 5-ethyl-4-methyl-1H-pyrazole-3-carboxylic acid in step (a). White solid. MS (ISP): 320.1 ([{$^{37}$Cl}M+H]$^+$), 318.1 ([{$^{35}$Cl}M+H]$^+$).

EXAMPLE 6 (COMPARATIVE EXAMPLE)

N-[4-[(2S)-Morpholin-2-yl] phenyl]-2-phenyl-1,3-thiazole-5-carboxamide

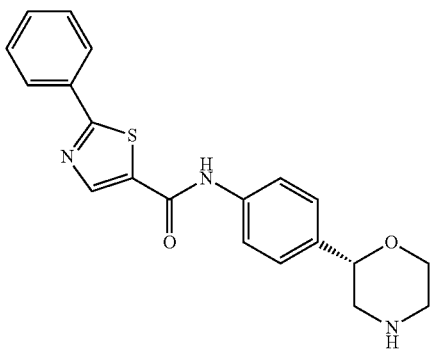

The title compound was obtained in analogy to example 1 using 2-phenylthiazole-5-carboxylic acid (CAS RN: 10058-38-5) in place of 5-ethyl-4-methyl-1H-pyrazole-3-carboxylic acid in step (a). White solid. MS (ISP): 366.1 ([M+H]$^+$).

EXAMPLE 7 (COMPARATIVE EXAMPLE)

2,6-Dichloro-N-[4-[(2S)-morpholin-2-yl]phenyl]pyridine-4-carboxamide

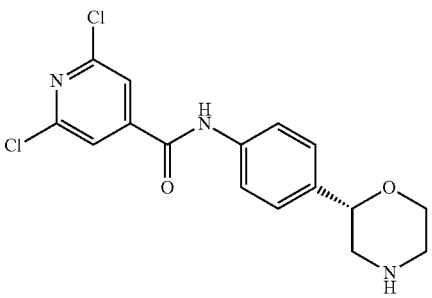

The title compound was obtained in analogy to example 1 using 2,6-dichloro-isonicotinic acid (CAS RN: 5398-44-7) in place of 5-ethyl-4-methyl-1H-pyrazole-3-carboxylic acid in step (a).

White solid. MS (ISP): 356.1 ([{$^{37}$Cl}M+H]$^+$), 354.1 ([{$^{37}$Cl$^{35}$Cl}M+H]$^+$), 352.1 ([{$^{35}$Cl}M+H]$^+$).

EXAMPLE 8 (COMPARATIVE EXAMPLE)

4-Methyl-N-[4-[(2S)-morpholin-2-yl] phenyl]-5-phenyl-1H-pyrazole-3-carboxamide

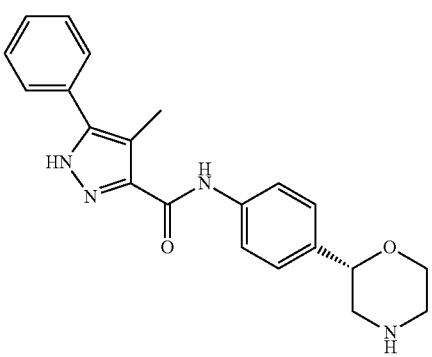 [SMILES: Cc1c(C(=O)Nc2ccc([C@H]3CNCCO3)cc2)n[nH]c1-c1ccccc1]

The title compound was obtained in analogy to example 1 using 4-methyl-5-phenyl-1H-pyrazole-3-carboxylic acid (CAS RN: 879770-33-9) in place of 5-ethyl-4-methyl-1H-pyrazole-3-carboxylic acid in step (a). White solid. MS (ISP): 363.2 ([M+H]$^+$).

EXAMPLE 9 (COMPARATIVE EXAMPLE)

5,6-Dichloro-N-[4-[(2S)-morpholin-2-yl]phenyl]pyridine-3-carboxamide

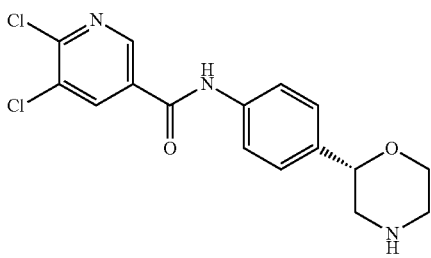 [SMILES: O=C(Nc1ccc([C@H]2CNCCO2)cc1)c1cnc(Cl)c(Cl)c1]

The title compound was obtained in analogy to example 1 using 5,6-dichloro-nicotinic acid (CAS RN: 41667-95-2) in place of 5-ethyl-4-methyl-1H-pyrazole-3-carboxylic acid in step (a). White solid. MS (ISP): 356.1 ([$\{^{37}Cl^{35}Cl\}$M+H]$^+$), 354.1 ([$\{^{37}Cl\}$M+H]$^+$), 352.1 ([$\{^{35}Cl\}$M+H]$^+$).

EXAMPLE 10 (COMPARATIVE EXAMPLE)

6-Cyano-N-[4-[(2S)-morpholin-2-yl]phenyl]pyridine-3-carboxamide

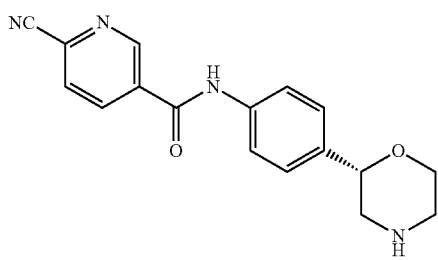

The title compound was obtained in analogy to example 1 using 6-cyano-nicotinic acid (CAS RN: 70165-31-0) in place of 5-ethyl-4-methyl-1H-pyrazole-3-carboxylic acid in step (a). White solid. MS (ISP): 309.1 ([M+H]$^+$).

EXAMPLE 11 (COMPARATIVE EXAMPLE)

N-[4-[(2S)-Morpholin-2-yl]phenyl]-6-(trifluoromethyl)pyridine-3-carboxamide

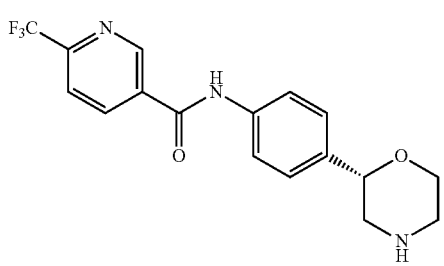 [SMILES: O=C(Nc1ccc([C@H]2CNCCO2)cc1)c1ccc(C(F)(F)F)nc1]

The title compound was obtained in analogy to example 1 using 6-(trifluoromethyl)nicotinic acid (CAS RN: 158063-66-2) in place of 5-ethyl-4-methyl-1H-pyrazole-3-carboxylic acid in step (a). White solid. MS (ISP): 352.2 ([M+H]$^+$).

EXAMPLE 12 (COMPARATIVE EXAMPLE)

5-Chloro-N-[4-[(2S)-morpholin-2-yl]phenyl]pyridine-2-carboxamide

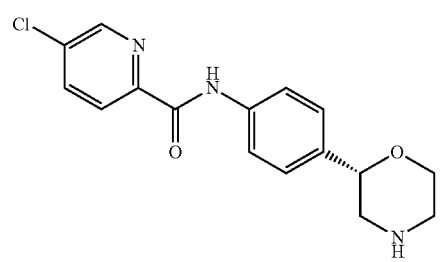

The title compound was obtained in analogy to example 1 using 5-chloro-picolinic acid (CAS RN: 86873-60-1) in place of 5-ethyl-4-methyl-1H-pyrazole-3-carboxylic acid in step (a). White solid. MS (ISP): 320.1 ([$\{^{37}Cl\}$M+H]$^+$), 318.2 ([$\{^{35}Cl\}$M+H]$^+$).

EXAMPLE 13 (COMPARATIVE EXAMPLE)

5-Chloro-N-[4-[(2S)-morpholin-2-yl]phenyl]pyridine-3-carboxamide

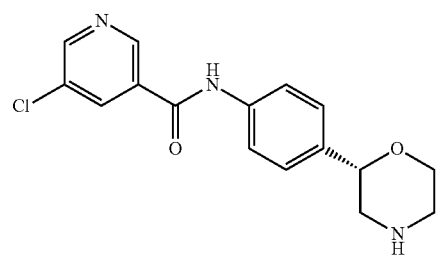 [SMILES: O=C(Nc1ccc([C@H]2CNCCO2)cc1)c1cncc(Cl)c1]

The title compound was obtained in analogy to example 1 using 5-chloro-nicotinic acid (CAS RN: 22620-27-5) in place of 5-ethyl-4-methyl-1H-pyrazole-3-carboxylic acid in step (a). White solid. MS (ISP): 320.1 ([$\{^{37}Cl\}$M+H]$^+$), 318.1 ([$\{^{35}Cl\}$M+H]$^+$).

EXAMPLE 14 (COMPARATIVE EXAMPLE)

2-Chloro-6-methyl-N-[4-[(2S)-morpholin-2-yl]phenyl]pyridine-4-carboxamide

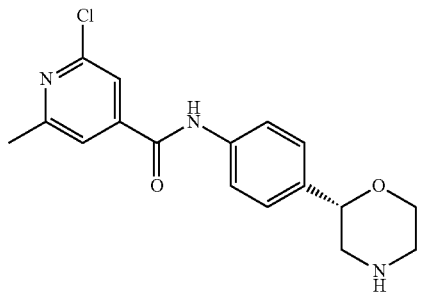

The title compound was obtained in analogy to example 1 using 2-chloro-6-methylpyridine-4-carboxylic acid (CAS RN: 25462-85-5) in place of 5-ethyl-4-methyl-1H-pyrazole-3-carboxylic acid in step (a). White solid. MS (ISP): 334.1 ([{$^{37}$Cl}M+H]$^+$), 332.1 ([{$^{35}$Cl}M+H]$^+$).

EXAMPLE 15 (COMPARATIVE EXAMPLE)

N-[4-[(2S)-Morpholin-2-yl]phenyl]-2-phenyl-1,3-oxazole-4-carboxamide

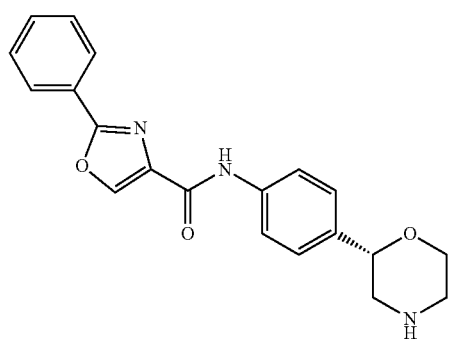 [SMILES: O=C(Nc1ccc([C@H]2CNCCO2)cc1)c1coc(-c2ccccc2)n1]

The title compound was obtained in analogy to example 1 using 2-phenyloxazole-4-carboxylic acid (CAS RN: 23012-16-0) in place of 5-ethyl-4-methyl-1H-pyrazole-3-carboxylic acid in step (a). White solid. MS (ISP): 350.2 ([M+H]$^+$).

EXAMPLE 16 (COMPARATIVE EXAMPLE)

N-[4-[(2S)-Morpholin-2-yl]phenyl]-2-phenyl-1,3-thiazole-4-carboxamide

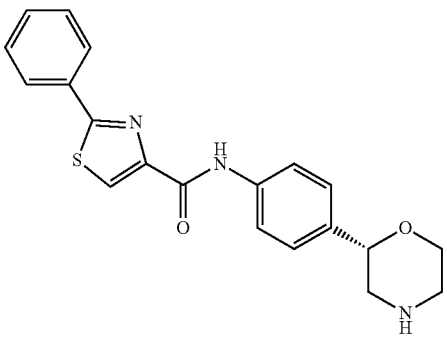 [SMILES: O=C(Nc1ccc([C@H]2CNCCO2)cc1)c1csc(-c2ccccc2)n1]

The title compound was obtained in analogy to example 1 using 2-phenylthiazole-4-carboxylic acid (CAS RN: 7113-10-2) in place of 5-ethyl-4-methyl-1H-pyrazole-3-carboxylic acid in step (a). White solid. MS (ISP): 366.1 ([M+H]$^+$).

EXAMPLE 17 (COMPARATIVE EXAMPLE)

2-Methyl-N-[4-[(2S)-morpholin-2-yl]phenyl]pyridine-4-carboxamide

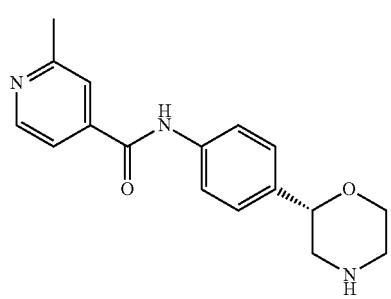 [SMILES: Cc1cc(C(=O)Nc2ccc([C@H]3CNCCO3)cc2)ccn1]

The title compound was obtained in analogy to example 1 using 2-methyl-isonicotinic acid (CAS RN: 4021-11-8) in place of 5-ethyl-4-methyl-1H-pyrazole-3-carboxylic acid in step (a). White solid. MS (ISP): 298.2 ([M+H]$^+$).

EXAMPLE 18 (COMPARATIVE EXAMPLE)

2,6-Dimethyl-N-[4-[(2S)-morpholin-2-yl]phenyl]pyridine-4-carboxamide

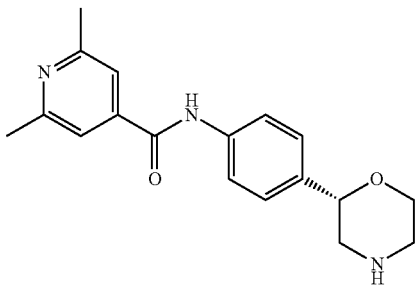 [SMILES: Cc1cc(C(=O)Nc2ccc([C@H]3CNCCO3)cc2)cc(C)n1]

The title compound was obtained in analogy to example 1 using 2,6-dimethyl-isonicotinic acid (CAS RN: 54221-93-1) in place of 5-ethyl-4-methyl-1H-pyrazole-3-carboxylic acid in step (a). White solid. MS (ISP): 312.2 ([M+H]$^+$).

EXAMPLE 19 (COMPARATIVE EXAMPLE)

N-[4-[(2S)-Morpholin-2-yl]phenyl]2-methyl-1,3-thiazole-4-carboxamide

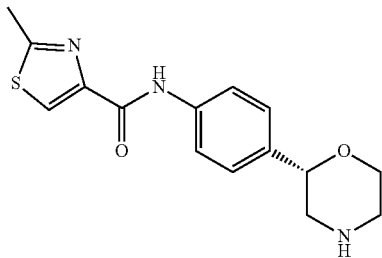 [SMILES: Cc1nc(C(=O)Nc2ccc([C@H]3CNCCO3)cc2)cs1]

The title compound was obtained in analogy to example 1 using 2-methylthiazole-4-carboxylic acid (CAS RN: 35272-15-2) in place of 5-ethyl-4-methyl-1H-pyrazole-3-carboxylic acid in step (a). White solid. MS (ISP): 304.1 ([M+H]$^+$).

EXAMPLE 20 (COMPARATIVE EXAMPLE)

N-[4-[(2S)-Morpholin-2-yl]phenyl]-1-phenylpyrazole-3-carboxamide

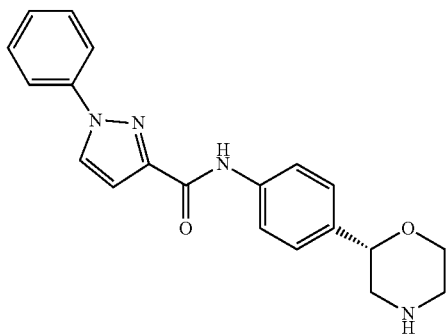 [SMILES: O=C(Nc1ccc([C@H]2CNCCO2)cc1)c1ccn(-c2ccccc2)n1]

The title compound was obtained in analogy to example 1 using 1-phenyl-1H-pyrazole-3-carboxylic acid (CAS RN: 4747-46-0) in place of 5-ethyl-4-methyl-1H-pyrazole-3-carboxylic acid in step (a). White solid. MS (ISP): 349.2 ([M+H]$^+$).

As mentioned above, the compound of the present invention has significant advantages over compounds of the prior art, which advantages are potent agonistic activity at the human TAAR1 receptor, selectivity against the dopamine transporter (DAT), selectivity against the hERG ion channel, and a low amphiphilic vector and thereby posing a low risk of causing drug-induced phospholipidosis (DIPL) (vide infra).

The following comparative data and comments may be provided to show the superiority advantages of the compound of formula I in comparison with known compounds of the prior art.

1. Pharmacological Effects and Therapeutic Potential of Partial Agonists of the Human Trace Amine-associated Receptor 1 (hTAAR1)

There is evidence of significant species differences in ligand-receptor interactions between rodent and human TAAR1[1]. Therefore, when selecting compounds for use as human therapeutics for the treatment of TAAR1-related diseases it is important to prioritize candidate compounds based on the potency of their functional activity at the human form of the TAAR1 receptor (hTAAR1). hTAAR1 is a G protein-coupled transmembrane receptor (GPCR), whereby ligands may function as antagonists, agonists, partial agonists or inverse agonists of the receptor. The compound of formula I and comparative examples have been tested in vitro for functional activity at hTAAR1, whereby the compound of formula I was found to be a partial agonist of hTAAR1. The experimentally determined hTAAR1 $EC_{50}$ values for the compound of formula I and a selection of comparative examples are shown in Table 1 (vide infra). The compound of example 1 has thereby been found, in particular, to be a potent partial agonist of hTAAR1 in vitro.

Ex vivo electrophysiology experiments in the ventral tegmental area and dorsal raphe nuclei showed that TAAR1 partial agonists enhanced DA and 5-HT neuron firing rates in wild-type mice[2,3], whereas full agonists like p-tyramine decreased firing rates[3,4]. However, both full and partial agonists have been shown to be protective against the rewarding and reinforcing effects of the psychostimulant cocaine[5]. Whereas full agonists like amphetamine induce negative feedback to blunt their own effect on DA and 5-HT systems[6,7], partial agonists might increase their effect on neuronal signal transmission by increasing firing rates via TAAR1. Because of these findings, and the reports that TAAR1 partial agonists have a richer in vivo pharmacology in rodents than full agonists[3,8], a strong body of preclinical evidence is emerging which suggests that TAAR1 partial agonists show highly promising potential for use as human therapeutics for the treatment of CNS diseases including, but not limited to, schizophrenia, bipolar disorder, depression, Parkinson's disease, as well as for the treatment of alcohol and drug addiction.

For instance, TAAR1 partial agonists are proposed to be superior to existing atypical antipsychotic drugs by displaying antipsychotic efficacy with the benefit of improved cognition and mood as well as with a reduced side effect profile (e.g. no induction of the metabolic syndrome which is seen with current antipsychotics)[3,8]. Other literature suggests possible indications include bipolar disorder,[8] drug addiction[5,9], and diabetesm[10].

Literature References

[1] Simmler, L. D.; Buchy, D.; Chaboz, S.; Hoener, M. C.; Liechti, M. E.; "In vitro characterization of psychoactive substances at rat, mouse and human trace amine-associated receptor 1". *J. Pharmacol. Exp. Ther.* 2016, Fast Forward article DOI: 10.1124/jpet.115.229765;

[2] Bradaia, A. et al.; "The selective antagonist EPPTB reveals TAAR1-mediated regulatory mechanisms in dopaminergic neurons of the mesolimbic system". *Proc. Nat. Acad. Sci. USA* 2009, 106, 20081-20086;

[3] Revel, F. G. et al.; "Trace amine-associated receptor 1 partial agonism reveals novel paradigm for neuropsychiatric therapeutics". *Biol. Psychiatry* 2012, 72, 934-942;

[4] Revel, F. G. et al.; "TAAR1 activation modulates monoaminergic neurotransmission, preventing hyperdopaminergic and hypoglutamatergic activity". *Proc. Nat. Acad. Sci. USA* 2011, 108, 8485-8490;

[5] Pei, Y.; Mortas, P.; Hoener, M. C.; Canales, J. J.; "Selective activation of the trace amine-associated receptor 1 decreases cocaine's reinforcing efficacy and prevents cocaine-induced changes in brain reward thresholds". *Prog. Neuro-Psychopharmacol. & Biol. Psychiatry* 2015, 63, 70-75;

[6] Lindemann, L. et al.; "Trace amine-associated receptor 1 modulates dopaminergic activity". *J. Pharmacol. Exp. Ther.* 2008, 324, 948-956;

[7] Di Cara, B. et al.; "Genetic deletion of trace amine 1 receptors reveals their role in auto-inhibiting the actions of ecstasy (MDMA)". *J. Neuroscience* 2011, 31, 16928-16940;

[8] Revel, F. G. et al.; "A new perspective for schizophrenia: TAAR1 agonists reveal antipsychotic- and antidepressant-like activity, improve cognition and control body weight". *Mol. Psychiatry* 2013, 18, 543-556;

[9] Pei, Y.; Lee, J.; Leo, D.; Gainetdinov, R. R.; Hoener, M. C.; Canales, J. J.; "Activation of the trace amine-associated receptor 1 prevents relapse to cocaine seeking". *Neuropsychopharmacology* 2014, 39, 2299-2308;

[10] Raab, S. et al.; "Incretin-like effects of small molecule trace amine-associated receptor 1 agonists". *Mol. Metabolism* 2016, 5, 47-56.

2. Dopamine Transporter (DAT) and Associated Liability for Drug Abuse and/or Addiction Potential The pharmacology of the dopamine transporter (DAT) has been implicated inter alia in the psychostimulatory effects and in the abuse liability and addiction mechanism of certain psychostimulant drugs such as cocaine and MDPV.[1-3] Therefore, for a new therapeutic intended for human use, it is desirable to avoid inhibition of, or interaction with, the dopamine transporter DAT in order to minimize the risk of abuse liability or potential for addiction.

For instance, evidence suggests that cocaine's reinforcing effects depend on its ability to rapidly block the dopamine transporter (DAT). In animal studies, dopamine reuptake inhibitors other than cocaine are also self-administered, with a relative potency that generally correlates positively with their potency in inhibiting the DAT, but not the serotonin or norepinephrine transporters (SERT, NET)[4-8]. Animals trained to self-administer cocaine will also self-administer direct dopamine agonists[9-11]. In addition, destruction of dopamine nerve terminals can lead to extinction of cocaine self-administration behavior[12,13], and these effects have been observed even when responding maintained by other reinforcers was preserved[14,15]. In humans, cocaine-induced "high" correlates with DAT occupancy in the brain[16].

To further test the hypothesis that DAT is essential to cocaine's reinforcing effects, a functional but "cocaine-insensitive" DAT was generated and expressed in mice[17, 18]. This mutant DAT demonstrated an 89-fold lower affinity for cocaine relative to wild-type DAT, and cocaine failed to increase extracellular dopamine in the nucleus accumbens, or to induce increases in locomotor activity, stereotypies, or conditioned place preferences, in knock-in (DATki) mice expressing this mutant DAT[18-20]. In addition, cocaine failed to serve as a positive reinforcer in these DATki mice, whereas food, d-amphetamine, and a direct dopamine agonist reliably maintained operant behavior in these mice, at levels comparable with wild-type mice[21]. Reintroduction of the cocaine-sensitive wild type DAT to brain areas including inter alia the ventral tegmental area (VTA) led to restoration of cocaine reward behavior in the DATki mice[22]. In conclusion, cocaine's ability to block DAT is sufficient to abolish its reinforcing effects in mice providing strong evidence that DAT blockade is critical for cocaine's reinforcing effects.

Therefore, taken together, these findings suggest that for a new therapeutic intended for human use, it is highly desirable to avoid inhibition of, or interaction with, the dopamine transporter DAT in order to minimize the risk of abuse liability or potential for addiction.

The measured in vitro DAT $K_i$ for a series of TAAR1 compounds are shown in Table 1 (vide infra). It has surprisingly been found that Example 1 is a significantly weaker ligand at DAT than other compounds, while simultaneously being a potent partial agonist of hTAAR1, and therefore the hTAAR1/DAT selectivity ratio for Example 1 is significantly higher than for other compounds.

Literature References

[1] Meil, W. M. and Boja, J. W.; "The dopamine transporter and addiction." Chapter 1, pp. 1-21 in *Neurochemistry of Abused Drugs* (Karch, S. B., Ed.), CRC Press (2008);

[2] Simmler, L. D. et al.; "Pharmacological characterization of designer cathinones in vitro". *Brit. J. Pharmacol.* 2013, 168, 458-470;

[3] Baumann, M. H.; Partilla, J. S.; Lehner, K. R.; "Psychoactive 'bath salts': not so soothing". *Eur. J. Pharmacol.* 2013, 698, 1-5;

[4] Ritz., M. C.; Lamb, R. J.; Goldberg, S. R.; Kuhar, M. J.; "Cocaine receptors on dopamine transporters are related to self-administration of cocaine". *Science* 1987, 237, 1219-1223;

[5] Bergmann., J.; Madras, B. K.; Johnson, S. E.; Spealman, R. D.; "Effects of cocaine and relared drugs in nonhuman primates. III. Self-administration by squirrel monkeys". *J. Pharmacol. Exp. Ther.* 1989, 251, 150-155;

[6] Howell., L. L. & Byrd, L. D.; "Serotonergic modulation of the behavioural effects of cocaine in the squirrel monkey". *J. Pharmacol. Exp. Ther.* 1995, 275, 1551-1559;

[7] Roberts, D. C. S. et al.; "Self-administration of cocaine analogs by rats". *Psychopharmacology* 1999, 144, 389-397;

[8] Wee, S. et al.; "Relationship between serotonergic activity and reinforcing effects of a series of amphetamine analogs". *J. Pharmacol. Exp. Ther.* 2005, 313, 848-854;

[9] Woolverton, W. L.; Goldberg, L. I.; Ginos, J. Z.; "Intravenous self-administration of dopamine receptor agonists by Rhesus monkeys". *J. Pharmacol. Exp. Ther.* 1984, 230, 678-683;

[10] Wise, R. A.; Murray, A.; Bozarth, M. A.; "Bromocriptine self-administration and bromocriptine-reinstatement of cocaine-trained and heroin-trained lever pressing in rats". *Psychopharmacology* 1990, 100, 355-360;

[11] Caine, S. B. & Koob, G. F.; "Modulation of cocaine self-administration in the rat through D-3 dopamine receptors". *Science* 1993, 260, 1814-1816;

[12] Roberts, D. C. S.; Corcoran, M. E.; Fibiger, H. C.; "On the role of ascending catecholaminergic systems in intravenous self-administration of cocaine". *Pharmacol. Biochem. Behaviour* 1977, 6, 615-620;

[13] Roberts, D. C. S.; Koob, G. F.; Klonoff, P.; Fibiger, H. C.; "Extinction and recovery of cocaine self-administration following 6-hydroxydopamine lesions of the nucleus accumbens". *Pharmacol. Biochem. Behaviour* 1980, 12, 781-787;

[14] Pettit, H. O.; Ettenberg, A.; Bloom, F. E.; Koob, G. F.; "Destruction of dopamine in the nucleus accumbens selectively attenuates cocaine but not heroin self-administration in rats". *Psychopharmacology* 1984, 84, 167-173;

[15] Caine, S. B. & Koob, G. F.; "Effects of mesolimbic dopamine depletion on responding maintained by cocaine and food". *J. Exp. Anal. Behavior* 1994, 61, 213-221;

[16] Volkow, N. D. et al.; "Relationship between subjective effects of cocaine and dopamine transporter occupancy". *Nature* 1997, 386, 827-830;

[17] Chen, R.; Han, D. D.; Gu, H. H.; "A triple mutation in the second transmembrane domain of mouse dopamine transporter markedly decreases sensitivity to cocaine and methylphenidate". *J. Neurochem.* 2005, 94, 352-359;

[18] Chen, R. et al.; "Abolished cocaine reward in mice with a cocaine-insensitive dopamine transporter". *Proc. Nat. Acad. Sci. USA* 2006, 103, 9333-9338;

[19] Tilley, M. R. & Gu, H. H.; "Dopamine transporter inhibition is required for cocaine-induced stereotypy". *Neuroreport* 2008, 19, 1137-1140;

[20] Tilley, M. R.; O'Neill, B.; Han, D. D.; Gu, H. H.; "Cocaine does not produce reward in absence of dopamine transporter inhibition". *Neuroreport* 2009, 20, 9-12;

[21] Thomsen, M.; Han, D. D.; Gu, H. H.; Caine, S. B.; "Lack of cocaine self-administration in mice expressing a cocaine-insensitive dopamine transporter". *J. Pharmacol. Exp. Ther.* 2009, 331, 204-211;

[22] Wu, H. et al.; "Restoration of cocaine stimulation and reward by reintroducing wild type dopamine transporter in adult knock-in mice with a cocaine-insensitive dopamine transporter". *Neuropharmacology* 2014, 86, 31-37.

3. hERG Blockade and Associated Liability for Cardiac QT Interval Prolongation

Minimization of the likelihood to cause drug-induced cardiac side effects is highly desirable for a therapeutic agent intended for safe use in humans, especially for a drug intended to be used for chronic treatment regimens. In recent years, regulatory authorities have delayed approval or imposed restrictions on the use of, and even denied approval or removed from the market, therapeutic agents prolonging the cardiac QT interval. The QT interval is the time from the beginning of the QRS complex to the end of the T wave of the electrocardiogram (ECG) and is a measure of the duration of ventricular depolarization and repolarization. Drugs prolonging the QT interval have been associated with a polymorphic ventricular tachycardia referred to as Torsades de Pointes (TdP). This arrhythmia can cause serious cardiovascular outcomes and can progress to irreversible ventricular fibrillation and death. The ICH S7B regulatory guideline[1] recommends an overall non-clinical strategy for evaluating cardiovascular risk of new molecular entities (NMEs) which includes the in vitro $IK_r$ assay [potassium current conducted by the human ether-a-go-go related gene (hERG)]. Inhibition of hERG was identified as the major mechanism for QT prolongation.[2] Therefore, the recommended minimal non-clinical QT interval de-risking strategy is to test representative compounds from a given chemical series in the in vitro hERG assay.[3] The goal is to select compounds causing no more than 20% hERG inhibition at concentrations at least 30-fold below the efficacious in vitro (or in vivo if available) concentration for therapeutic activity. In the case of TAAR1 agonists, the hTAAR1 $EC_{50}$ can be considered as the relevant in vitro concentration predictive of therapeutic activity (vide supra). Therefore it is desirable to select TAAR1 agonists where the ratio hERG $IC_{20}$/hTAAR1 $EC_{50}$ is at least 30-fold.

The measured in vitro hERG $IC_{20}$ and $IC_{50}$ for a series of TAAR1 compounds are shown in Table 1 (vide infra).

Basic compounds in particular are known to be especially prone to causing potent inhibition of the hERG channel.[4] All of the TAAR1 compounds bear the same morpholino head group, therefore all compounds are expected to be similarly basic. The basic moiety is required for agonist activity at hTAAR1. It has surprisingly been found that Example 1 is a significantly weaker hERG channel inhibitor than comparative compounds, and therefore the hERG $IC_{20}$/hTAAR1 $EC_{50}$ ratio for Example 1 is significantly higher than the recommended 30-fold minimum.

Literature References

[1] ICH Guideline. "The nonclinical evaluation of the potential for delayed ventricular repolarization (QT interval prolongation) by human pharmaceuticals (S7B)" issued as CPMP/ICH/423/02, adopted by CHMP in May 2005; http://www.ich.org/products/guidelines/safety/safety-single/article/the-non-clinical-evaluation-of-the-potential-for-delayed-ventricular-repolarization-qt-interval-pro.html

[2] Redfern, W. S.; Carlsson, L.; Davis, A. S.; Lynch, W. G.; MacKenzie, I.; Palethorpe, S.; Siegl, P.K.; Strang, I; Sullivan, A. T.; Wallis, R.; Camm, A.J.; Hammond, T. G.; "Relationships between preclinical cardiac electrophysiology, clinical QT interval prolongation and torsade de pointes for a broad range of drugs: evidence for a provisional safety margin in drug development". *Cardiovasc. Res.* 2003, 58, 32-45;

[3] Helliwell, R. M.: "Potassium Channels". *Methods in Molecular Biology* (Totowa, N.J., United States) 2008, 491, 279-295;

[4] Zolotoy, A. B.; Plouvier, B. P.; Beatch, G. B.; Hayes, E. S.; Wall, R. A.; Walker, M. J. A.; "Physicochemical determinants for drug-induced blockade of hERG potassium channels: Effect of charge and charge shielding". *Curr. Med. Chem.—Cardiovascular & Hematological Agents* 2003, 1, 225-241.

4. Amphiphilicity and Associated Liability for Drug-Induced Phospholipidosis (DIPL)

Phospholipidosis (PLD) is a lysosomal storage disorder characterized by the excess accumulation of phospholipids in tissues[1][2][3] Many cationic amphiphilic drugs, including anti-depressants, antianginal, antimalarial, and cholesterol-lowering agents, are reported to cause drug-induced phospholipidosis (DIPL) in animals and humans. The mechanisms of DIPL involve trapping or selective uptake of DIPL drugs within the lysosomes and acidic vesicles of affected cells. Drug-trapping is followed by a gradual accumulation of drug-phospholipid complexes within the internal lysosomal membranes. The increase in undigested materials results in the abnormal accumulation of multi-lammellar bodies (myeloid bodies) in tissues. Although phospholipidosis is primarily considered to be a storage disorder, with some compounds the storage disorder is known to be associated with inflammation and necrosis leading to functional impairment of the affected tissues. It is therefore highly desirable that a therapeutic drug should not pose a risk for causing DIPL. This is especially true in the case of medicines intended for chronic use, for instance, drugs intended for the treatment of chronic psychiatric disorders such as schizophrenia, bipolar disorder or depression, or drugs intended for the treatment of chronic metabolic disorders such as diabetes.

DIPL is an adverse effect known to be particularly associated with cationic amphiphilic drugs (CAD).[4] To avoid DIPL either the basic $pK_a$ (basic $pK_a$<6.3) or the amphiphilicity ($\Delta\Delta G_{am}$>−6 kJ mol$^{-1}$) of a compound has to be reduced (i.e. $\Delta\Delta G_{am}$ needs to be increased).[5] A compound is classified as DIPL negative if either the basic $pK_a$ value is below 6.3 or the amphiphilicity is above $\Delta\Delta G_{am}$=−6 kJ mol$^{-1}$. The amphiphilicity for a given compound can be calculated in silico directly from the molecular structural formula,[6] and therefore the predicted risk for DIPL for that compound can also be calculated in silico,[5] whereby the prediction algorithm uses a DIPL risk classification defined according to the following criteria, which are based on parameters extracted from a computational training set comprising experimentally determined phospholipidosis results for a large set of compounds:

AMPHIPHILIC VECTOR>−5.0 kJ/mol and BPKA1<=5.60 results in NEGATIVE DIPL prediction;

−7.0 kJ/mol<AMPHIPHILIC VECTOR<−5.0 kJ/mol and/or 7.0 >BPKA1>5.60 results in BORDERLINE DIPL prediction;

AMPHIPHILIC VECTOR<−7.0 kJ/mol and BPKA1>=7.00 results in POSITIVE DIPL prediction.

The calculated amphiphilicities ($\Delta\Delta G_{am}$ in kJ mol$^{-1}$) as well as the in silico DIPL risk predictions (negative/borderline/positive) for a series of TAAR1 compounds are shown in Table 1 (vide infra).

All of the TAAR1 compounds bear the same morpholino head group, therefore the basic $pK_a$ of all compounds is very similar and clearly above 6.3. The basic moiety is required for agonist activity at hTAAR1. Therefore, the only way to avoid DIPL is to reduce the lipophilicity of the backbone of the molecules. It has surprisingly been found that for Example 1 the lipophilicity is reduced significantly more than expected based on the results for similar compounds, and therefore the amphiphilicity of Example 1 is clearly reduced and, as a consequence, this compound is not predicted to cause DIPL.

Literature References

[1] Anderson, N.; Borlak, J.; "Drug-induced phospholipidosis". *FEBS Lett.* 2006, 580, 5533-540;
[2] Reasor, M. J.; Hastings, K. L.; Ulrich, R. G.; "Drug-induced phospholipidosis: issues and future directions". *Expert Opin. Drug Safety* 2006, 5, 567-83;
[3] Nonoyama, T.; Fukuda, R.; "Drug induced phospholipidosis pathological aspects and its prediction". *J. Toxicol. Pathol.* 2008, 21, 9-24;
[4] Lullmann, H.; Lullmann-Rauch, R.; Wassermann, O; "Lipidosis induced by amphiphilic cationic drugs." *Biochem. Pharmacol.* 1978, 27, 1103-8;
[5] Fischer, H.; Atzpodien, E. A.; Csato, M; Doessegger, L.; Lenz, B.; Schmitt, G.; Singer, T.; "In silico assay for assessing phospholipidosis potential of small drug like molecules: training, validation and refinement using several datasets." *J. Med. Chem.* 2012, 55, 126-139;
[6] Fischer, H.; Kansy, M.; Bur, D.; "CAFCA: a novel tool for the calculation of amphiphilic properties of charged drug molecules". *Chimia* 2000, 54, 640-645.

The compounds were investigated in accordance with the tests given hereinafter.

Materials and Methods

Human TAAR1

For the construction of expression plasmids the coding sequences of human TAAR 1 were amplified from genomic DNA essentially as described by Lindemann et al.[14]. The Expand High Fidelity PCR System (Roche Diagnostics) was used with 1.5 mM Mg$^{2+}$ and purified PCR products were cloned into pCR2.1-TOPO cloning vector (Invitrogen) following the instructions of the manufacturer. PCR products were subcloned into the pIRESneo2 vector (BD Clontech, Palo Alto, Calif.), and expression vectors were sequence verified before introduction in cell lines.

HEK293 cells (ATCC # CRL-1573) were cultured essentially as described by Lindemann et al. (2005). For the generation of stably transfected cell lines HEK293 cells were transfected with the pIRESneo2 expression plasmids containing the TAAR coding sequences (described above) with Lipofectamine 2000 (Invitrogen) according to the instructions of the manufacturer, and 24 hrs post transfection the culture medium was supplemented with 1 mg/ml G418 (Sigma, Buchs, Switzerland). After a culture period of about 10 d clones were isolated, expanded and tested for responsiveness to trace amines (all compounds purchased from Sigma) with the cAMP Biotrak Enzyme immunoassay (EIA) System (Amersham) following the non-acetylation EIA procedure provided by the manufacturer. Monoclonal cell lines which displayed a stable EC$_{50}$ for a culture period of 15 passages were used for all subsequent studies.

cAMP measurements were performed as described previously (Revel et al., *Proc. Natl. Acad. Sci. USA* 2011, 108, 8485-8490). In brief, cells that expressed human TAAR1 were plated on 96-well plates (BIOCOAT 6640; Becton Dickinson, Allschwil, Switzerland) and incubated for 20 h at 37° C. Prior to stimulation of the cells with a broad concentration range of agonists for 30 min at 37° C., the cells were washed with PBS and preincubated with PBS that contained 1 mM 3-isobutyl-1-methylxanthine for 10 min at 37° C. and 5% CO$_2$. Stimulation with 0.2% DMSO was set as the basal level, and the effect of 30 µM β-PEA was set as the maximal response. Subsequently, the cells were lysed, and cAMP assays were performed according to the manufacturer's instructions (cAMP kit; Upstate/Millipore, Schaffhausen, Switzerland). Finally, the plates were read with a luminometer (1420 Multilabel counter; PerkinElmer, Schwerzenbach, Switzerland), and the amount of cAMP was calculated. The results were obtained from at least three independent experiments. Experiments were run in duplicate or triplicate. EC$_{50}$ values are presented as mean ±standard deviation (in µM). The E$_{max}$ value for the functional activity data at TAAR1 describes the degree of functional activity compared with 100% for the endogenous ligand and full agonist (β-PEA.

Human DAT

Binding to dopamine transporter (DAT) in vitro. Human embryonic kidney (HEK) 293 cells (Invitrogen, Zug, Switzerland) stably transfected with human DAT were cultured. The cells were collected and washed three times with phosphate-buffered saline (PBS). The pellets were frozen at −80° C. The pellets were then resuspended in 400 ml of 20 mM HEPES-NaOH, pH 7.4, that contained 10 mM EDTA at 4° C. After homogenization with a Polytron (Kinematica, Lucerne, Switzerland) at 10000 rotations per minute (rpm) for 15 s, the homogenates were centrifuged at 48000×g for 30 min at 4° C. Aliquots of the membrane stocks were frozen at −80° C. All assays were performed at least three times. The test compounds were diluted in 20 ml of binding buffer (252 mM NaCl, 5.4 mM KCl, 20 mM $Na_2HPO_4$, 3.52 mM $KH_2PO_4$, pH 7.4) and 10 point dilution curves were made and transferred to 96-well white polystyrene assay plates (Sigma-Aldrich, Buchs, Switzerland). [$^3$H]-WIN35,428 (~86 Ci /mmol; Perkin-Elmer) was the radioligand for the DAT assay and had a $K_d$ of 12 nM. Fifty microliters of [$^3$H]-WIN35,428 (~40 nM concentration) was added to each well of the hDAT assay plates, targeting a final [$^3$H]-WIN35428 concentration of 10 nM. Twenty microliters of binding buffer alone in the assay plate defined the total binding, whereas binding in the presence of 10 µM indatraline defined nonspecific binding. Frozen DAT membrane stocks were thawed and resuspended to a concentration of approximately 0.04 mg protein/ml binding buffer (1:1 diluted in $H_2O$) using a polytron tissue homogenizer. The membrane homogenates (40 µg/ml) were then lightly mixed for 5-30 min with polyvinyl toluene (PCT) wheat germ agglutinin-coated scintillation proximity assay (WGASPA; Amersham Biosciences) beads at 7.7 mg beads/ml homogenate. One hundred thirty microliters of the membrane/bead mixture were added to each well of the assay plate that contained radioligand and test compounds (final volume in each well, 200 µl) to start the assay, which was incubated for approximately 2 h at room temperature with agitation. The assay plates were then counted in the PVT SPA counting mode of a Packard Topcount. Fifty microliters of the [$^3$H]-WIN35428 stocks were counted in 5 ml of ReadySafe scintillation cocktail (Beckman Industries) on a Packard 1900CA liquid scintillation counter to determine the total counts added to the respective assays. Non-linear regression was used to fit the data to sigmoid curves and determine $IC_{50}$ values for binding and uptake. $K_i$ values for binding and uptake were calculated using the following Cheng-Prusoff equation: $K_i = IC_{50}/(1+[S]/K_m)$.

Human ERG (hERG)

The whole-cell patch-clamp technique was used to investigate the effects of the test items on hERG (human-ether-a-go-go related gene) potassium channels in stably transfected CHO cells near physiological temperature (36±1° C.). The effects of compounds on hERG $K^+$-current parameters were evaluated at 4 concentrations (0.3-3-30-300 µM) in at least 3 CHO cells stably expressing the hERG channel. For electrophysiological measurements cells were seeded onto 35 mm sterile culture dishes containing 2 ml culture medium without Hygromycin B. Cells were cultivated at a density that enabled single cells (without visible connections to neighbouring cells) to be measured. Cells were incubated at 37° C. in a humidified atmosphere with 5% $CO_2$ (rel. humidity about 95%). The cells were continuously maintained in and passaged in sterile culture flasks containing nutrient mixture F-12 (DMEM/F-12 with L-Glutamine) supplemented with 10% foetal bovine serum and 10% penicillin/streptomycin solution. Every day at least three cells were treated with a selective IKr blocker (E-4031, reference substance) to assure accuracy of the method. The 35 mm culture dishes upon which cells were seeded at a density allowing single cells to be recorded were placed on the dish holder of the microscope and continuously perfused (at approximately 1 ml/min) with the bath solution (sodium chloride 150 mM, potassium chloride 4 mM, calcium chloride 1.2 mM, magnesium chloride 1 mM, HEPES 10 mM, pH (NaOH) 7.4) at near physiological temperature (36±1° C.). After formation of a Gigaohm seal between the patch electrodes and individual hERG stably transfected CHO cells (pipette resistance range: 2.0 MΩ-7.0 Mω; seal resistance range: >1 Gω) the cell membrane across the pipette tip was ruptured to assure electrical access to the cell interior (whole-cell patch-configuration). In case the quality of the seal was poor, the process of seal formation was repeated with a different cell and a new pipette. As soon as a stable seal was established, hERG outward tail currents were measured upon depolarization of the cell membrane to −40 mV for 50 ms followed by 500 ms at +20 mV (activation of channels) from a holding potential of −80 mV and upon subsequent repolarization to −40 mV for 500 ms. This voltage protocol was run at least 10 times at intervals of 10 s. If current density was judged to be too low for measurement, another cell was recorded. Once control recordings have been accomplished, cells were continuously perfused with a bath solution containing the test items. During wash-in of the test item the voltage protocol indicated above was run continuously again at 10 s intervals until the steady-state level of block was reached. The four test item concentrations of the compound were applied sequentially to 3 cells in a cumulative manner. As hERG tail currents were inhibited by the test item, the concentration-response curve was generated and ICso value calculated. Based on the $IC_{50}$ value the $IC_{20}$ was estimated. Each concentration of the test item was analyzed in three experiments (n=3).

Amphiphilic Vector ($\Delta\Delta G_{am}$) Calculation and in silico DIPL Prediction Amphiphilic vector ($\Delta\Delta G_{am}$) and in silico DIPL prediction were computationally determined from the molecular structural formula for the compound of formula I and comparative compounds according to the published algorithms (Fischer, H.; Kansy, M.; Bur, D.; "CAFCA: a novel tool for the calculation of amphiphilic properties of charged drug molecules". Chimia 2000, 54, 640-645; Fischer, H.; Atzpodien, E. A.; Csato, M; Doessegger, L.; Lenz, B.; Schmitt, G.; Singer, T.; "In silico assay for assessing phospholipidosis potential of small drug like molecules: training, validation and refinement using several datasets." J. Med. Chem. 2012, 55, 126-139).

The compound of formula I has partial agonist activity on hTAAR1 ($EC_{50}$ in µM), binding affinity at hDAT ($K_i$ in µM), and channel blocking activity at hERG ($IC_{20}$ and $IC_{50}$ in µM) as shown in Table 1. Table 1 also shows the calculated amphiphilic vector ($\Delta\Delta G_{am}$ in kJ $mol^{-1}$) and in silico phospholipidosis estimation (negative/positive/borderline prediction for in vitro DIPL and in vivo DIPL) for the compound of formula I and comparative compounds, as calculated using the procedure described above.

TABLE 1

| Example No | Structure | hTAAR1 EC$_{50}$ (μM) | hTAAR1 efficacy* (%) | hERG IC$_{50}$ (μM) | hERG IC$_{20}$ (μM) | Ratio hERG IC$_{20}$/ hTAAR1 EC$_{50}$ | Phospho-lipidosis ΔΔG$_{am}$ (kJ mol$^{-1}$) | in silico Phospho-lipidosis (in vitro) | in silico Phospho-lipidosis (in vivo) | DAT K$_i$ (μM) | Ratio DAT K$_i$/ hTAAR1 EC$_{50}$ |
|---|---|---|---|---|---|---|---|---|---|---|---|
| 1 | 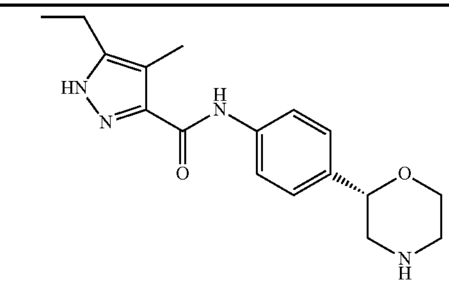 | 0.0585 | 42 | 216.60 | 36.20 | 619 | −3.47 | NEGATIVE | NEGATIVE | 27.53 | 471 |
| 2 | 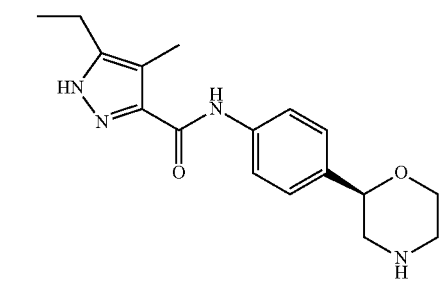 [SMILES: CCc1[nH]nc(C(=O)Nc2ccc([C@@H]3CNCCO3)cc2)c1C] | 0.2632 | 38 | — | — | — | — | — | — | — | — |
| 3 | 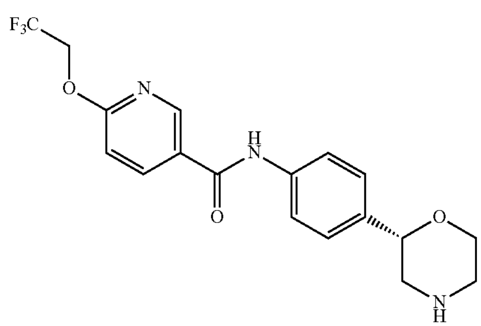 [SMILES: O=C(Nc1ccc([C@H]2CNCCO2)cc1)c1ccc(OCC(F)(F)F)nc1] | 0.0377 | 45 | 9.84 | 1.97 | 52 | −6.3 | POSITIVE | BORDERLINE | 17.43 | 462 |

TABLE 1-continued

| Example No | Structure | hTAAR1 EC$_{50}$ (μM) | hTAAR1 efficacy* (%) | hERG IC$_{50}$ (μM) | hERG IC$_{20}$ (μM) | Ratio hERG IC$_{20}$/ hTAAR1 EC$_{50}$ | Phospho- lipidosis ΔΔG$_{am}$ (kJ mol$^{-1}$) | in silico Phospho- lipidosis (in vitro) | in silico Phospho- lipidosis (in vivo) | DAT K$_i$ (μM) | Ratio DAT K$_i$/ hTAAR1 EC$_{50}$ |
|---|---|---|---|---|---|---|---|---|---|---|---|
| 4 | 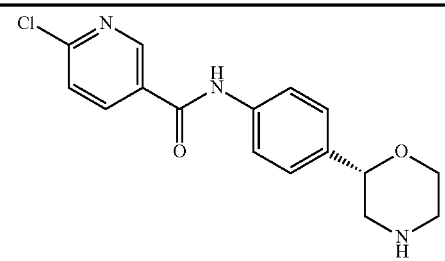 | 0.0619 | 49 | 49.67 | 12.42 | 201 | -5.31 | NEGATIVE | BORDERLINE | 2.50 | 40 |
| 5 | 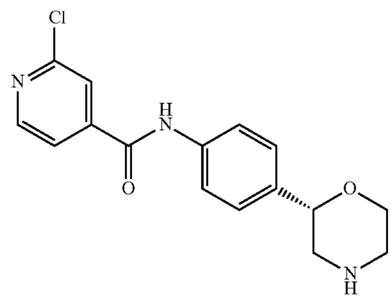 [SMILES: O=C(Nc1ccc([C@H]2CNCCO2)cc1)c1ccnc(Cl)c1] | 0.0656 | 40 | 81.71 | 22.16 | 338 | -5.9 | NEGATIVE | BORDERLINE | 1.52 | 23 |
| 6 | 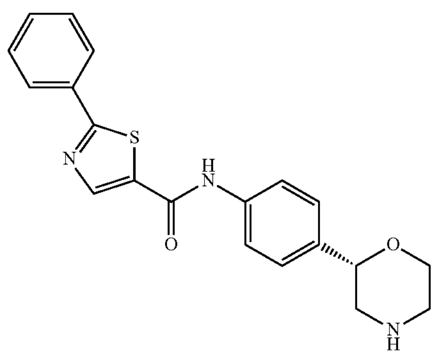 [SMILES: O=C(Nc1ccc([C@H]2CNCCO2)cc1)c1cnc(-c2ccccc2)s1] | 0.08 | 30 | 1.31 | 0.38 | 5 | -8.46 | POSITIVE | POSITIVE | 5.93 | 74 |

TABLE 1-continued

| Example No | Structure | hTAAR1 EC$_{50}$ (μM) | hTAAR1 efficacy* (%) | hERG IC$_{50}$ (μM) | hERG IC$_{20}$ (μM) | Ratio hERG IC$_{20}$/ hTAAR1 EC$_{50}$ | Phospho- lipidosis ΔΔG$_{am}$ (kJ mol$^{-1}$) | in silico Phospho- lipidosis (in vitro) | in silico Phospho- lipidosis (in vivo) | DAT K$_i$ (μM) | Ratio DAT K$_i$/ hTAAR1 EC$_{50}$ |
|---|---|---|---|---|---|---|---|---|---|---|---|
| 7 | 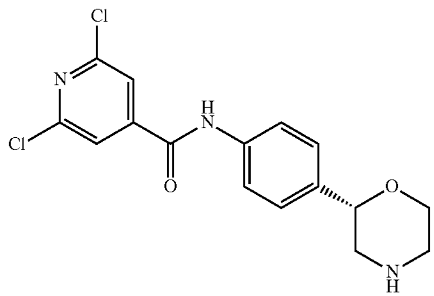 [SMILES: O=C(Nc1ccc([C@H]2CNCCO2)cc1)c1cc(Cl)nc(Cl)c1] | 0.0849 | 57 | 11.39 | 3.67 | 43 | −7.41 | POSITIVE | POSITIVE | 0.79 | 9 |
| 8 | 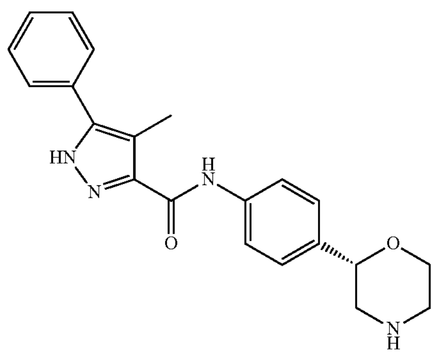 [SMILES: Cc1c(C(=O)Nc2ccc([C@H]3CNCCO3)cc2)n[nH]c1-c1ccccc1] | 0.1086 | 33 | 10.78 | 3.01 | 28 | −4.89 | NEGATIVE | NEGATIVE | 9.77 | 90 |
| 9 | 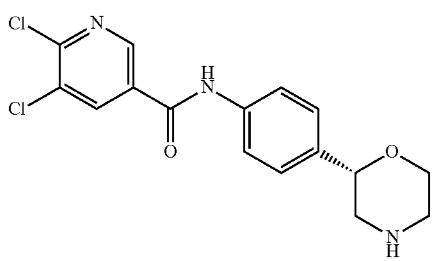 [SMILES: O=C(Nc1ccc([C@H]2CNCCO2)cc1)c1cnc(Cl)c(Cl)c1] | 0.1437 | 32 | 4.46 | 1.14 | 8 | −8.83 | POSITIVE | POSITIVE | 0.48 | 3 |

TABLE 1-continued

| Example No | Structure | hTAAR1 EC$_{50}$ (μM) | hTAAR1 efficacy* (%) | hERG IC$_{50}$ (μM) | hERG IC$_{20}$ (μM) | Ratio hERG IC$_{20}$/ hTAAR1 EC$_{50}$ | Phospho- lipidosis ΔΔG$_{am}$ (kJ mol$^{-1}$) | in silico Phospho- lipidosis (in vitro) | in silico Phospho- lipidosis (in vivo) | DAT K$_i$ (μM) | Ratio DAT K$_i$/ hTAAR1 EC$_{50}$ |
|---|---|---|---|---|---|---|---|---|---|---|---|
| 10 | NC-pyridine-C(O)NH-phenyl-morpholine | 0.1837 | 38 | 31.72 | 5.78 | 31 | -3.11 | NEGATIVE | NEGATIVE | 11.30 | 62 |
| 11 | F$_3$C-pyridine-C(O)NH-phenyl-morpholine | 0.2027 | 46 | 17.42 | 2.59 | 13 | -6.18 | POSITIVE | BORDERLINE | 2.33 | 12 |
| 12 | Cl-pyridine-C(O)NH-phenyl-morpholine | 0.2119 | 40 | 14.26 | 3.21 | 15 | -6.59 | POSITIVE | BORDERLINE | 1.78 | 8 |

TABLE 1-continued

| Example No | Structure | hTAAR1 EC$_{50}$ (µM) | hTAAR1 efficacy* (%) | hERG IC$_{50}$ (µM) | hERG IC$_{20}$ (µM) | Ratio hERG IC$_{20}$/ hTAAR1 EC$_{50}$ | Phospholipidosis ΔΔG$_{am}$ (kJ mol$^{-1}$) | in silico Phospholipidosis (in vitro) | in silico Phospholipidosis (in vivo) | DAT K$_i$ (µM) | Ratio DAT K$_i$/ hTAAR1 EC$_{50}$ |
|---|---|---|---|---|---|---|---|---|---|---|---|
| 13 | 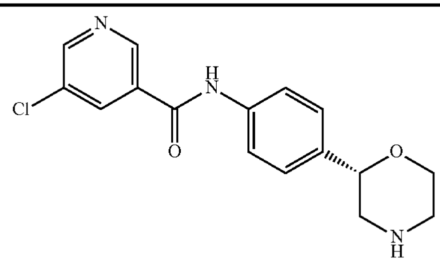 | 0.4045 | 37 | 66.04 | 9.14 | 23 | −6.23 | POSITIVE | BORDERLINE | 1.31 | 3 |
| 14 | 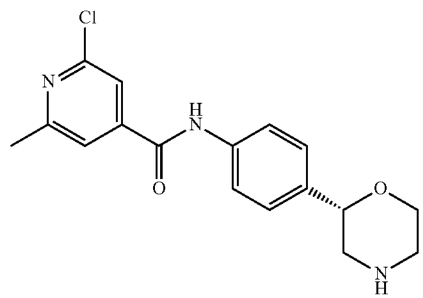 [SMILES: Cc1cc(C(=O)Nc2ccc([C@H]3CNCCO3)cc2)cc(Cl)n1] | 0.4467 | 53 | 73.18 | 21.63 | 48 | −6.96 | POSITIVE | BORDERLINE | 7.32 | 16 |
| 15 | 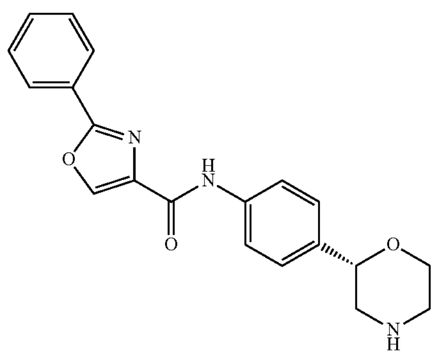 [SMILES: O=C(Nc1ccc([C@H]2CNCCO2)cc1)c1coc(-c2ccccc2)n1] | 0.6632 | 35 | 9.65 | 2.40 | 4 | −7.4 | POSITIVE | POSITIVE | >26.1 | >39 |

TABLE 1-continued

| Example No | Structure | hTAAR1 EC$_{50}$ (μM) | hTAAR1 efficacy* (%) | hERG IC$_{50}$ (μM) | hERG IC$_{20}$ (μM) | Ratio hERG IC$_{20}$/ hTAAR1 EC$_{50}$ | Phospholipidosis ΔΔG$_{am}$ (kJ mol$^{-1}$) | in silico Phospholipidosis (in vitro) | in silico Phospholipidosis (in vivo) | DAT K$_i$ (μM) | Ratio DAT K$_i$/ hTAAR1 EC$_{50}$ |
|---|---|---|---|---|---|---|---|---|---|---|---|
| 16 | 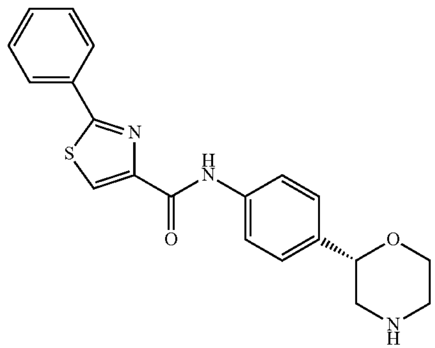 [SMILES: O=C(Nc1ccc([C@H]2CNCCO2)cc1)c1csc(-c2ccccc2)n1] | 0.666 | 35 | 8.98 | 3.35 | 5 | -8.48 | POSITIVE | POSITIVE | 16.22 | 24 |
| 17 | 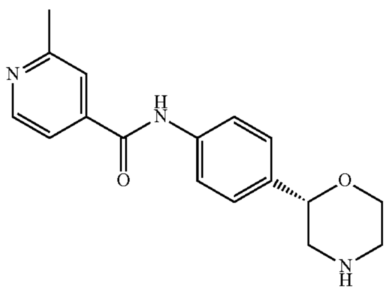 [SMILES: Cc1cc(C(=O)Nc2ccc([C@H]3CNCCO3)cc2)ccn1] | 0.6727 | 45 | 518.2 | 129.55 | 193 | -4.53 | NEGATIVE | NEGATIVE | 10.32 | 15 |
| 18 | 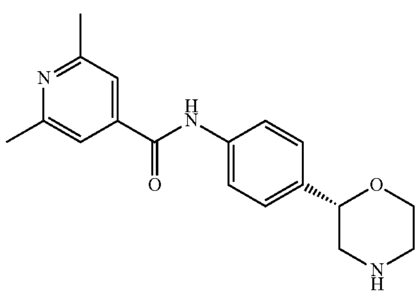 [SMILES: Cc1cc(C(=O)Nc2ccc([C@H]3CNCCO3)cc2)cc(C)n1] | 0.8271 | 63 | 711.5 | 146.78 | 177 | -5.82 | NEGATIVE | BORDERLINE | >26.1 | >32 |

TABLE 1-continued

| Example No | Structure | hTAAR1 EC$_{50}$ (μM) | hTAAR1 efficacy* (%) | hERG IC$_{50}$ (μM) | hERG IC$_{20}$ (μM) | Ratio hERG IC$_{20}$/ hTAAR1 EC$_{50}$ | Phospho-lipidosis ΔΔG$_{am}$ (kJ mol$^{-1}$) | in silico Phospho-lipidosis (in vitro) | in silico Phospho-lipidosis (in vivo) | DAT K$_i$ (μM) | Ratio DAT K$_i$/ hTAAR1 EC$_{50}$ |
|---|---|---|---|---|---|---|---|---|---|---|---|
| 19 | 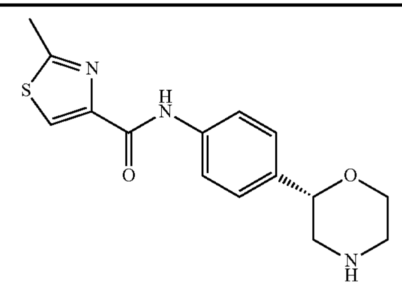 | 1.025 | 32 | 60.47 | 8.32 | 8 | −4.59 | NEGATIVE | NEGATIVE | 21.9 | 21 |
| 20 | 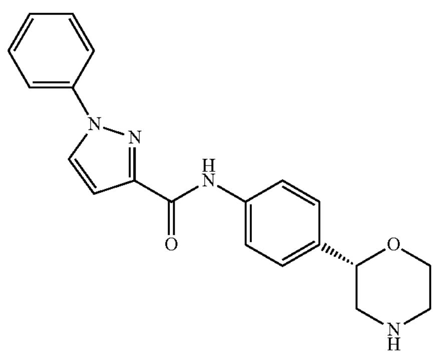 [SMILES: O=C(Nc1ccc([C@H]2CNCCO2)cc1)c1ccn(-c2ccccc2)n1] | 2.480 | 59 | 10.75 | 2.49 | 1 | −5.37 | NEGATIVE | BORDERLINE | >26.1 | >11 |

*% agonist activity for hTAAR1 is reported on a scale calibrated such that effect of the endogeneous ligand β-phenylethylamine = 100% agonism It has surprisingly been found that the compound of formula I (example 1) displays an overall superior combination of properties in terms of potent agonist activity at hTAAR1, high selectivity against hDAT, high selectivity against hERG, low amphiphilic vector and consequently low phospholipidosis risk compared to other TAAR1 compounds of the prior art.

Inspection of Table 1 reveals that example 1 has potent partial agonist activity at hTAAR1 (EC$_{50}$=0.059 µM), is highly selective against hDAT (K$_i$=27.5 µM; selectivity ratio=471-fold versus hTAAR1 EC$_{50}$), is highly selective against hERG (IC$_{20}$=36.2 µM; selectivity ratio=619-fold versus hTAAR1 EC$_{50}$) and has a low amphiphilic vector ($\Delta\Delta G_{am}$=−3.47 kJ mol$^{-1}$) well below the threshold of concern for phospholipidosis (in silico DIPL risk prediction=negative).

Inspection of Table 1 reveals that close analogues of example 1 have inferior properties compared to example 1 in one or more regards.

For instance, comparative example 2, which is the R enantiomer of example 1, is less potent at hTAAR1 (EC$_{50}$=0.2632 µM), which teaches that the S configuration of absolute stereochemistry, as in example 1, is preferred in order to obtain higher potency at hTAAR1.

Comparative example 3 is significantly more potent at hERG (IC$_{20}$=1.97 µM; selectivity ratio=52-fold versus hTAAR1 EC$_{50}$) and also has a significantly higher amphiphilic vector ($\Delta\Delta G_{am}$=−6.3 kJ mol$^{-1}$) and thus a positive DIPL prediction.

Comparative example 4 is significantly more potent at DAT (K$_i$=2.5 µM; selectivity ratio=40-fold versus hTAAR1 EC$_{50}$) and also has a higher amphiphilic vector ($\Delta\Delta G_{am}$=−5.3 kJ mol$^{-1}$) and thus a borderline DIPL prediction.

Comparative example 5 is significantly more potent at DAT (K$_i$=1.5 µM; selectivity ratio=23-fold versus hTAAR1 EC$_{50}$) and also has a higher amphiphilic vector ($\Delta\Delta G_{am}$=−5.9 kJ mol$^{-1}$) and thus a borderline DIPL prediction.

Comparative example 6 is significantly more potent at hERG (IC$_{20}$=0.38 µM; selectivity ratio=5-fold versus hTAAR1 EC$_{50}$), is more potent at DAT (K$_i$=5.9 µM; selectivity ratio=74-fold versus hTAAR1 EC$_{50}$) and also has a significantly higher amphiphilic vector ($\Delta\Delta G_{am}$=−8.46 kJ mol$^{-1}$) and thus a positive DIPL prediction.

Comparative example 7 is significantly more potent at hERG (IC$_{20}$=3.57 µM; selectivity ratio=43-fold versus hTAAR1 EC$_{50}$), is significantly more potent at DAT (K$_i$=0.79 µM; selectivity ratio=9-fold versus hTAAR1 EC$_{50}$) and also has a significantly higher amphiphilic vector ($\Delta\Delta G_{am}$=−7.41 kJ mol$^{-1}$) and thus a positive DIPL prediction.

Comparative example 8 is significantly more potent at hERG (IC$_{20}$=3.01 µM; selectivity ratio=28-fold versus hTAAR1 EC$_{50}$).

Comparative example 9 is less potent at hTAAR1 (EC$_{50}$=0.144 µM), is significantly more potent at hERG (IC$_{20}$=1.14 µM; selectivity ratio=8-fold versus hTAAR1 EC$_{50}$), is significantly more potent at DAT (K$_i$=0.48 µM; selectivity ratio=3-fold versus hTAAR1 EC$_{50}$) and also has a significantly higher amphiphilic vector ($\Delta\Delta G_{am}$=−8.83 kJ mol$^{-1}$) and thus a positive DIPL prediction.

Comparative example 10 is less potent at hTAAR1 (EC$_{50}$=0.184 µM) and is more potent at hERG (IC$_{20}$=5.78 µM; selectivity ratio=31-fold versus hTAAR1 EC$_{50}$).

Comparative example 11 is less potent at hTAAR1 (EC$_{50}$=0.203 µM), is significantly more potent at hERG (IC$_{20}$=2.59 µM; selectivity ratio=13-fold versus hTAAR1 EC$_{50}$), is significantly more potent at DAT (K$_i$=2.33 µM; selectivity ratio=12-fold versus hTAAR1 EC$_{50}$) and also has a significantly higher amphiphilic vector ($\Delta\Delta G_{am}$=−6.18 kJ mol$^{-1}$) and thus a positive DIPL prediction.

Comparative example 12 is less potent at hTAAR1 (EC$_{50}$=0.212 µM), is significantly more potent at hERG (IC$_{20}$=3.21 µM; selectivity ratio=15-fold versus hTAAR1 EC$_{50}$), is significantly more potent at DAT (K$_i$=1.78 µM; selectivity ratio=8-fold versus hTAAR1 EC$_{50}$) and also has a significantly higher amphiphilic vector ($\Delta\Delta G_{am}$=−6.59 kJ mol$^{-}$) and thus a positive DIPL prediction.

Comparative example 13 is significantly less potent at hTAAR1 (EC$_{50}$=0.405 µM), is more potent at hERG (IC$_{20}$=9.14 µM; selectivity ratio=23-fold versus hTAAR1 EC$_{50}$), is significantly more potent at DAT (K$_i$=1.31 µM; selectivity ratio=3-fold versus hTAAR1 EC$_{50}$) and also has a significantly higher amphiphilic vector ($\Delta\Delta G_{am}$=−6.23 kJ mol$^{-1}$) and thus a positive DIPL prediction.

Comparative example 14 is significantly less potent at hTAAR1 (EC$_{50}$=0.447 µM), is significantly more potent at DAT (K$_i$=7.32 µM; selectivity ratio=16-fold versus hTAAR1 EC$_{50}$) and also has a significantly higher amphiphilic vector ($\Delta\Delta G_{am}$=−6.96 kJ mol$^{-1}$) and thus a positive DIPL prediction.

Comparative example 15 is significantly less potent at hTAAR1 (EC$_{50}$=0.663 µM), is significantly more potent at hERG (IC$_{20}$=2.40 µM; selectivity ratio=4-fold versus hTAAR1 EC$_{50}$) and also has a significantly higher amphiphilic vector ($\Delta\Delta G_{am}$=−7.4 kJ mol$^{-1}$) and thus a positive DIPL prediction.

Comparative example 16 is significantly less potent at hTAAR1 (EC$_{50}$=0.666 µM), is significantly more potent at hERG (IC$_{20}$=3.35 µM; selectivity ratio=5-fold versus hTAAR1 EC$_{50}$) and also has a significantly higher amphiphilic vector ($\Delta\Delta G_{am}$=−8.48 kJ mol$^{-1}$) and thus a positive DIPL prediction.

Comparative example 17 is significantly less potent at hTAAR1 (EC$_{50}$=0.673 µM) and is more potent at DAT (K$_i$=10.32 µM; selectivity ratio=15-fold versus hTAAR1 EC$_{50}$).

Comparative example 18 is significantly less potent at hTAAR1 (EC$_{50}$=0.827 µM) and also has a higher amphiphilic vector ($\Delta\Delta G_{am}$=−5.82 kJ mol$^{-1}$) and thus a borderline DIPL prediction.

Comparative example 19 is significantly less potent at hTAAR1 (EC$_{50}$=1.025 µM) and is more potent at hERG (IC$_{20}$=8.32 µM; selectivity ratio=8-fold versus hTAAR1 EC$_{50}$).

Finally, comparative example 20 is significantly less potent at hTAAR1 (EC$_{50}$=2.48 µM), is significantly more potent at hERG (IC$_{20}$=2.49 µM; selectivity ratio=1-fold versus hTAAR1 EC$_{50}$) and also has a higher amphiphilic vector ($\Delta\Delta G_{am}$=−5.37 kJ mol$^{-1}$) and thus a borderline DIPL prediction.

Therefore, taking all of the data in Table 1 into consideration, the compound of formula I (example 1) is the overall most preferred compound for the intended use as a safe and effective therapeutic agent for treatment in humans of TAAR1-related disorders, especially for the treatment of chronic CNS disorders, such as depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse, addiction and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders. The most preferred disorders are schizophrenia, bipolar disorder or depression.

The compound of formula I and the pharmaceutically acceptable salts of the compound of formula I can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compound of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing the compound of formula I and/or pharmaceutically acceptable acid addition salts and, if desired, one or more other therapeutically valuable substances into a galenical administration form together with one or more therapeutically inert carriers.

The most preferred indications in accordance with the present invention are those which include disorders of the central nervous system, for example the treatment or prevention of depression, schizophrenia and bipolar disorders.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

| Tablet Formulation (Wet Granulation) | | | | | |
|---|---|---|---|---|---|
| Item | Ingredients | | mg/tablet | | |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Capsule Formulation | | | | | |
|---|---|---|---|---|---|
| Item | Ingredients | | mg/capsule | | |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

The invention claimed is:

1. A compound of formula I:

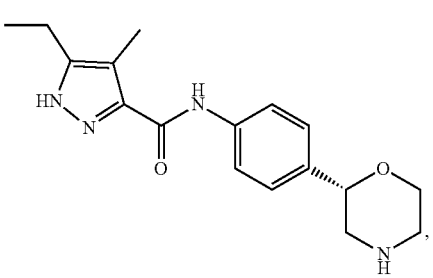

which is a 5-ethyl-4-methyl-N-[4-[(2S) morpholin-2-yl]phenyl]-1H-pyrazole-3-carboxamide, or a pharmaceutically suitable acid addition salt thereof.

2. The compound of formula I,

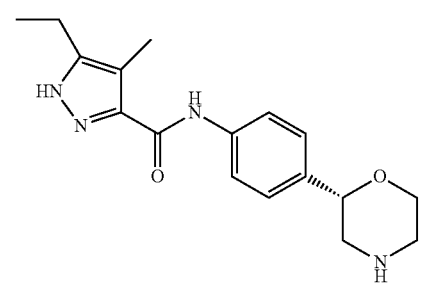

which is 5-ethyl-4-methyl-N-[4-[(2S)morpholin-2-yl]phenyl]-1H-pyrazole-3-carboxamide.

3. A process for the manufacture of the compound of formula I according to claim 1, which process comprises
   a) cleaving off the N-protecting group (PG) from compounds of formula

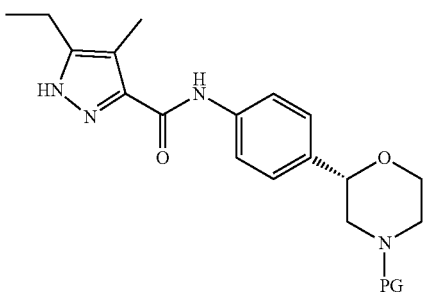

to a compound of formula

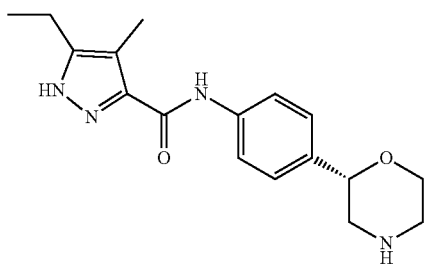

I wherein PG is a N-protecting group, selected from —C(O)O-tert-butyl (BOC), and, if desired, converting the compounds obtained into pharmaceutically acceptable acid addition salts.

4. A pharmaceutical composition comprising the compound of formula I according to claim 1 and pharmaceutically acceptable excipients.

5. A method for the treatment of a disease or disorder selected from the group consisting of depression, anxiety disorders, bipolar disorder, attention deficit hyperactivity disorder (ADHD), stress-related disorders, schizophrenia, Parkinson's disease, Alzheimer's disease, epilepsy, migraine, hypertension, substance abuse, addiction, eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders, the method comprising administering an effective amount of a compound of claim 1.

6. A method for the treatment of a disease or disorder selected from the group consisting of depression, anxiety disorders, bipolar disorder, attention deficit hyperactivity disorder (ADHD), stress-related disorders, schizophrenia, Parkinson's disease, Alzheimer's disease, epilepsy, migraine, hypertension, substance abuse, addiction, eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders, the method comprising administering an effective amount of a compound of claim 2.

7. The method of claim 5, wherein the disease or disorder is depression.

8. The method of claim 6, wherein the disease or disorder is depression.

9. The method of claim 5, wherein the disease or disorder is bipolar disorder.

10. The method of claim 6, wherein the disease or disorder is bipolar disorder.

11. The method of claim 5, wherein the disease or disorder is schizophrenia.

12. The method of claim 6, wherein the disease or disorder is schizophrenia.

13. The method of claim 5, wherein the disease or disorder is substance abuse.

14. The method of claim 6, wherein the disease or disorder is substance abuse.

15. The method of claim 5, wherein the disease or disorder is addiction.

16. The method of claim 6, wherein the disease or disorder is addiction.

17. The method of claim 5, wherein the disease or disorder is an eating disorder.

18. The method of claim 6, wherein the disease or disorder is an eating disorder.

19. The method of claim 5, wherein the disease or disorder is diabetes.

20. The method of claim 6, wherein the disease or disorder is diabetes.

21. An oral pharmaceutical preparation comprising the compound of formula I according to claim 1, wherein the oral pharmaceutical preparation is in a form selected from the group consisting of tablets, coated tablets, dragées, hard and soft gelatin capsules, solutions, emulsions or suspensions.

22. An oral pharmaceutical preparation comprising the compound of formula I according to claim 2, wherein the oral pharmaceutical preparation is in a form selected from the group consisting of tablets, coated tablets, dragées, hard and soft gelatin capsules, solutions, emulsions or suspensions.

* * * * *